(12) United States Patent
Almalki

(10) Patent No.: US 9,012,846 B2
(45) Date of Patent: Apr. 21, 2015

(54) HANDHELD DEVICE WITH SURFACE REFLECTION ESTIMATION

(71) Applicant: Research In Motion Limited, Waterloo (CA)

(72) Inventor: Nazih Almalki, Waterloo (CA)

(73) Assignee: BlackBerry Limited, Waterloo (CA)

( * ) Notice: Subject to any disclaimer, the term of this patent is extended or adjusted under 35 U.S.C. 154(b) by 215 days.

(21) Appl. No.: 13/684,325

(22) Filed: Nov. 23, 2012

(65) Prior Publication Data

US 2014/0146304 A1    May 29, 2014

(51) Int. Cl.
*G01N 21/55* (2014.01)

(52) U.S. Cl.
CPC ...................... *G01N 21/55* (2013.01)

(58) Field of Classification Search
USPC ........... 250/338.1, 339.11; 356/237.2, 3, 445, 356/601
See application file for complete search history.

(56) References Cited

U.S. PATENT DOCUMENTS

| 2002/0193080 | A1 | 12/2002 | Komsi et al. |
| 2007/0009135 | A1* | 1/2007 | Ishiyama ...................... 382/103 |
| 2007/0268481 | A1* | 11/2007 | Raskar et al. ................. 356/218 |
| 2008/0006762 | A1 | 1/2008 | Fadell et al. |
| 2012/0133790 | A1 | 5/2012 | Sams |

OTHER PUBLICATIONS

Extended Europeans Search Report dated Apr. 5, 2013 issued in connection with corresponding EP Application No. 12194101.7.

* cited by examiner

*Primary Examiner* — Mark R Gaworecki
(74) *Attorney, Agent, or Firm* — Ridout & Maybee LLP

(57) ABSTRACT

Estimating reflectance of a surface adjacent a handheld electronic device having a orientation sensor and a light sensor, including estimating a location of the handheld electronic device relative to the surface in dependence on information from the orientation sensor; measuring light from the surface with the light sensor; and estimating a reflectance of the surface in dependence on the estimated location and measured light.

20 Claims, 16 Drawing Sheets

HANDHELD DEVICE WITH SURFACE REFLECTION ESTIMATION

TECHNICAL FIELD

The present disclosure relates generally to a method and handheld electronic device which estimates the reflectance of a surface that the device is facing.

BACKGROUND

Handheld electronic devices, such as mobile communication devices, can provide a number of features and applications including, for example, a phone application, media player application, mapping application, calendar application, email application, instant messaging (IM) application, text messaging application (e.g., for sending and receiving short message service (SMS) messages), and other applications. A number of these applications generate notification messages for a device user. In some situations, it may be desirable to reflect information from the device off of a reflective surface.

BRIEF DESCRIPTION OF THE DRAWINGS

Like reference numerals are used in the drawings to denote like elements and features.

DETAILED DESCRIPTION OF EXAMPLE EMBODIMENTS

The embodiments described herein generally relate to handheld electronic devices. Examples of handheld electronic devices include mobile (wireless) communication devices such as pagers, cellular phones, Global Positioning System (GPS) navigation devices and other satellite navigation devices, smartphones, wireless organizers, personal digital assistants and wireless-enabled tablet computers. The handheld electronic device may be a portable electronic device without wireless communication capabilities such as a handheld electronic game device, digital photograph album, digital camera and video recorder such as a camcorder. The portable electronic devices could have a touchscreen display, a mechanical keyboard in addition to a touchscreen display, or a conventional non-touchscreen display with a mechanical keyboard. These examples are intended to be non-limiting.

According to one example there is described a method of estimating reflectance of a surface adjacent a handheld electronic device having a orientation sensor and a light sensor, including estimating a location of the handheld electronic device relative to the surface in dependence on information from the orientation sensor; measuring reflected light from the surface with the light sensor; and estimating a reflectance of the surface in dependence on the estimated location and measured light. A handheld electronic device of performing the method is also described.

Figure 1:
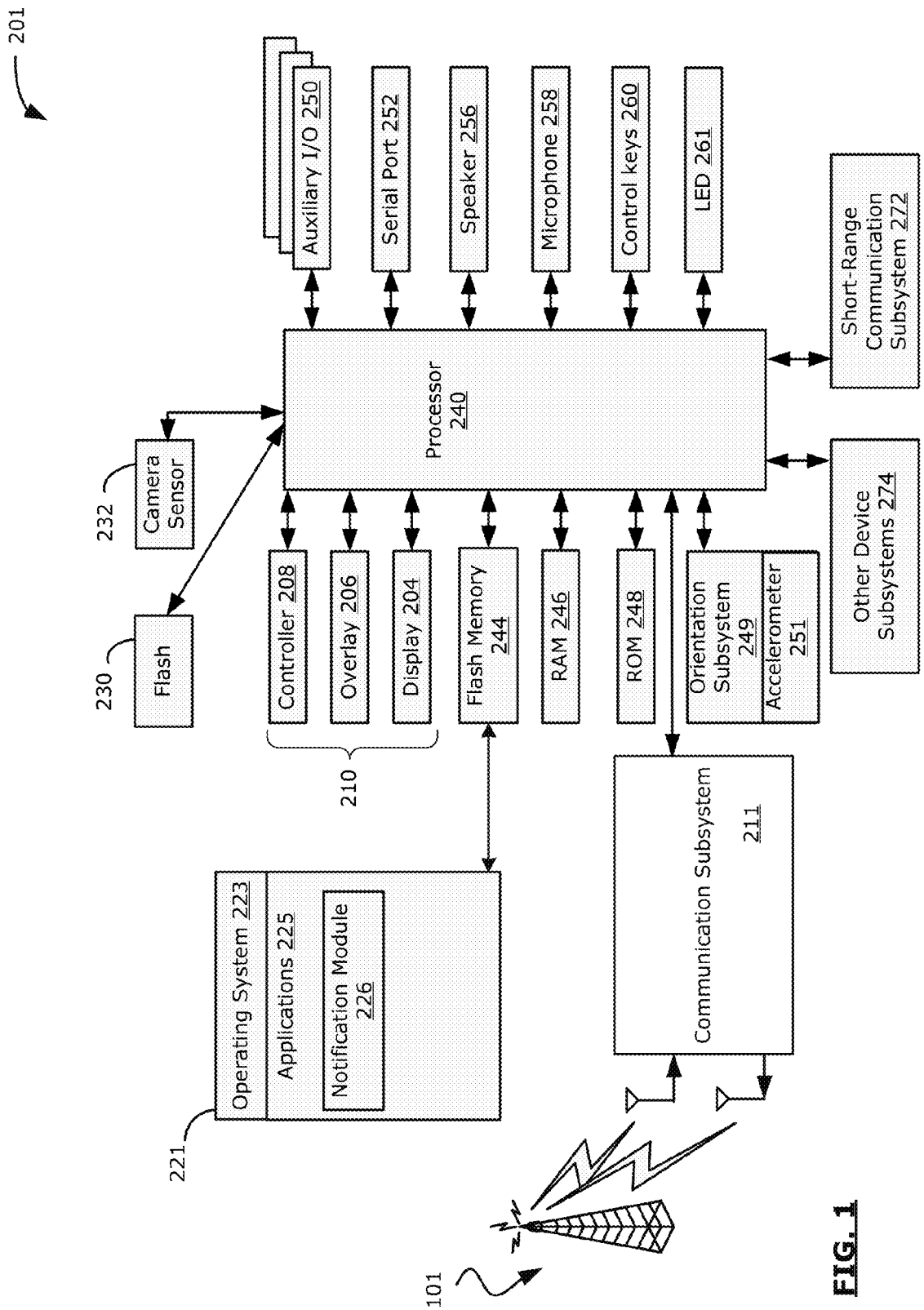
FIG. 1 is a block diagram illustrating a handheld electronics device in the form of a mobile communication device in accordance with one example embodiment of the present disclosure.

Reference is now made to FIG. 1 which illustrates a handheld electronics device in the form of a mobile communication device 201 to which example embodiments described in the present disclosure can be applied. The mobile communication device 201 is a two-way communication device having at least data and possibly also voice communication capabilities, and the capability to communicate with other computer systems, for example, via the Internet. Depending on the functionality provided by the mobile communication device 201, in various embodiments the device may be a data communication device, a multiple-mode communication device configured for both data and voice communication, a smartphone, a mobile telephone, a tablet style-computer or a PDA (personal digital assistant) enabled for wireless communication, or a computer system with a wireless modem.

The mobile communication device 201 includes a controller comprising at least one processor 240 such as a microprocessor which controls the overall operation of the mobile communication device 201, and a wireless communication subsystem 211 for exchanging radio frequency signals with the wireless network 101. The processor 240 interacts with the communication subsystem 211 which performs communication functions. The processor 240 interacts with additional device subsystems including a display screen 204, such as a liquid crystal display (LCD) screen, with a touch-sensitive input surface or overlay 206 connected to an electronic controller 208 that together make up a touchscreen display 210. The touch-sensitive overlay 206 and the electronic controller 208 provide a touch-sensitive input device and the processor 240 interacts with the touch-sensitive overlay 206 via the electronic controller 208. The device 201 could include other input devices such as a keyboard or keypad, navigational tool (input device), or both. The navigational tool could be a clickable/depressible trackball or scrollwheel. The other input devices could be included in addition to, or instead of, the touchscreen display 210.

The processor 240 interacts with additional device subsystems including a camera sensor 232 (which may for example include a charge coupled device) and camera flash 230, flash memory 244, random access memory (RAM) 246, read only memory (ROM) 248, auxiliary input/output (I/O) subsystems 250, data port 252 such as serial data port, such as a Universal Serial Bus (USB) data port, speaker 256, microphone 258, control keys 260, light emitting diode (LED) 261, short-range communication subsystem 272, an orientation subsystem 249 and other device subsystems generally designated as 274. Some of the subsystems shown in FIG. 1 perform communication-related functions, whereas other subsystems may provide "resident" or on-device functions.

The mobile communication device 201 may communicate with any one of a plurality of fixed transceiver base stations of the wireless network 101 within its geographic coverage area. The mobile communication device 201 may send and receive communication signals over the wireless network 101 after a network registration or activation procedures have been completed.

The processor 240 operates under stored program control and executes software modules 221 stored in memory such as persistent memory, for example, in the flash memory 244. As illustrated in FIG. 1, the software modules 221 comprise operating system software 223 and software applications 225. A notification module 226 provides instructions for the processor 240 to operate the notification message privacy viewing functions described herein. Notification module 226 may, among other things, each be implemented through standalone software applications, or combined together in one or more of the operating system 223 or other software applications 225. The functions performed by the module 226 may be realized as a plurality of independent elements, rather than a single integrated element, and any one or more of these elements may be implemented as parts of other software applications 225 or operating system software 223.

Those skilled in the art will appreciate that the software modules 221 or parts thereof may be temporarily loaded into volatile memory such as the RAM 246. The RAM 246 is used for storing runtime data variables and other types of data or information, as will be apparent to those skilled in the art. Although specific functions are described for various types of memory, this is merely one example, and those skilled in the art will appreciate that a different assignment of functions to types of memory could also be used.

The software applications 225 may include a range of applications, including, for example, an address book application, a messaging application, a calendar application, and/or a notepad application. In some embodiments, the software applications 225 include an email message application, one or more instant messaging applications, text messaging applications, a push content viewing application, a voice communication (i.e. telephony) application and a map application. Each of the software applications 225 may include layout information defining the placement of particular fields and graphic elements (e.g. text fields, input fields, icons, etc.) in the user interface (i.e. the display screen 204) according to the application.

A predetermined set of applications that control basic device operations, including data and possibly voice communication applications will normally be installed on the mobile communication device 201 during or after manufacture. Additional applications and/or upgrades to the operating system 223 or software applications 225 may also be loaded onto the mobile communication device 201 through the wireless network 101, the auxiliary I/O subsystem 250, the serial port 252, the short-range communication subsystem 272, or other suitable subsystem 274 other wireless communication interfaces. The downloaded programs or code modules may be permanently installed, for example, written into the program memory (i.e. the flash memory 244), or written into and executed from the RAM 246 for execution by the processor 240 at runtime.

The mobile communication device 201 may provide two principal modes of communication: a data communication mode and an optional voice communication mode. In the data communication mode, a received data signal such as a text message, an email message, or Web page download will be processed by the communication subsystem 211 and input to the processor 240 for further processing. For example, a downloaded Web page may be further processed by a browser application or an email message may be processed by an email message application and output to the display 242. A user of the mobile communication device 201 may also compose data items, such as email messages, for example, using the touch-sensitive overlay 206 in conjunction with the display device 204 and possibly the control buttons 260 and/or the auxiliary I/O subsystems 250. These composed items may be transmitted through the communication subsystem 211 over the wireless network 101.

In the voice communication mode, the mobile communication device 201 provides telephony functions and operates as a typical cellular phone. The overall operation is similar, except that the received signals would be output to the speaker 256 and signals for transmission would be generated by a transducer such as the microphone 258. The telephony functions are provided by a combination of software/firmware (i.e., the voice communication module) and hardware (i.e., the microphone 258, the speaker 256 and input devices). Alternative voice or audio I/O subsystems, such as a voice message recording subsystem, may also be implemented on the mobile communication device 201. Although voice or audio signal output is typically accomplished primarily through the speaker 256, the display device 204 may also be used to provide an indication of the identity of a calling party, duration of a voice call, or other voice call related information.

The orientation subsystem 249 comprises at least one sensor which is coupled to the processor 240 and which is controlled by one or a combination of a monitoring circuit and operating software. The sensor has a sensing element which detects acceleration from motion and/or gravity. The sensor generates and outputs an electrical signal representative of the detected acceleration. Changes in movement of the portable electronic device 100 result in changes in acceleration which produce corresponding changes in the electrical signal output of the sensor. The sensor may be an accelerometer 251, such as a three-axis accelerometer having three mutual orthogonally sensing axes. The accelerometer 251 may be digital or analog depending on the embodiment. The accelerometer 251 may be utilized to detect acceleration of the portable electronic device 201, such as a direction of gravitational forces or gravity-induced reaction forces. Other types of motion sensors may be used by the orientation subsystem 223 in addition to, or instead of, an accelerometer. The other motion sensors may comprise a proximity sensor, gyroscope, or both, which detect changes in the proximity and orientation of portable electronic device 201.

Figure 2:
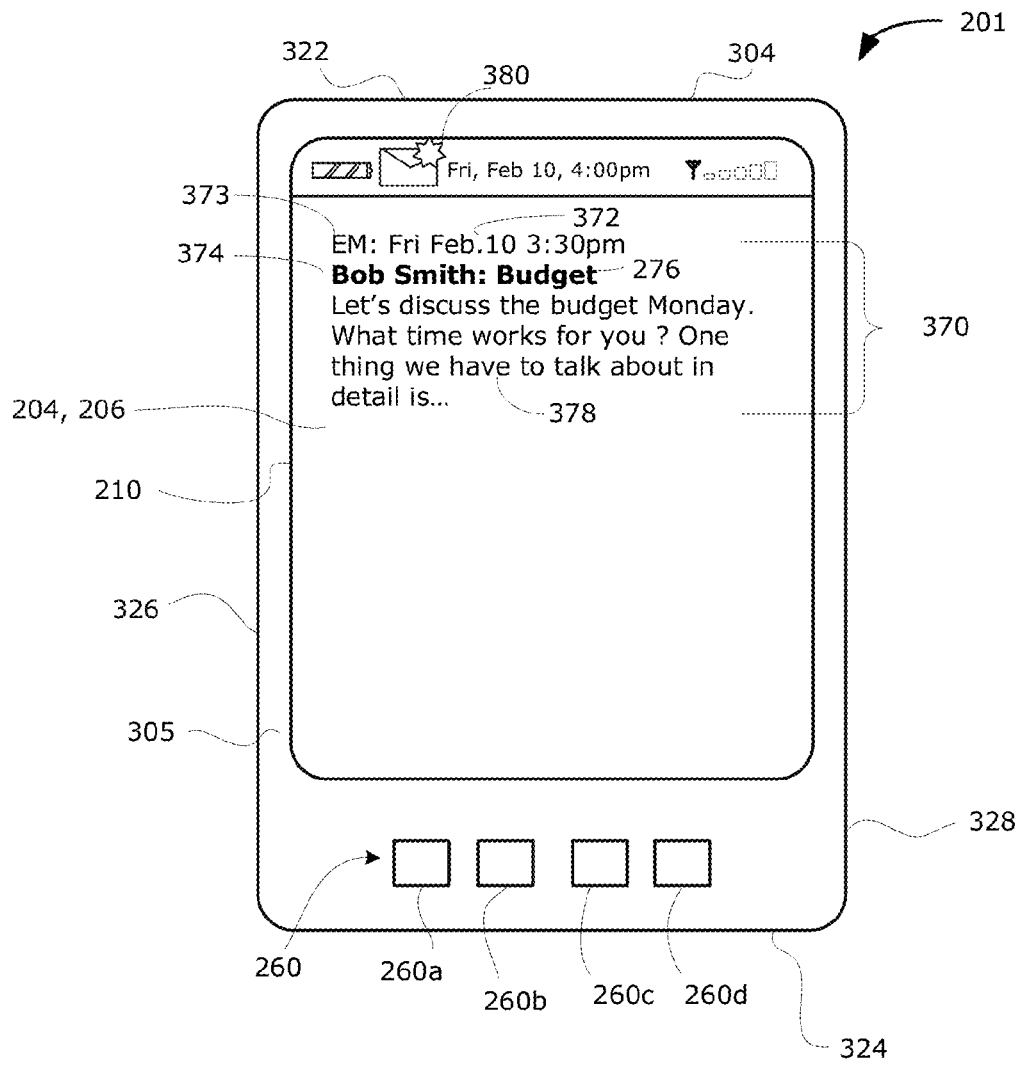
FIG. 2 is a front view of the mobile communications device of FIG. 1 in a portrait orientation.

Referring now to FIG. 2, the construction of the device 201 will be described in more detail. The device 201 includes a rigid case 304 for housing the components of the device 201 that is configured to be held or cradleable in a user's hand or hands while the device 201 is in use. The touchscreen display 210 is mounted within a front face 305 of the case 304 so that the case 304 frames the touchscreen display 210 with a generally planar display surface of the display screen 204 and the touchscreen overlay 206 facing forward for user-interaction therewith. The case 304 has top and bottom edges designated by references 322, 324 respectively, and left and right edges designated by references 326, 328 respectively which extend transverse to the top and bottom edges 322, 324. In the shown embodiment of FIG. 2, the case 304 (and device 201) is elongate having a length, defined between the top and bottom edges 322, 324, longer than a width, defined between the left and right edges 326, 328. Other device dimensions and form factors are also possible.

Figure 3:
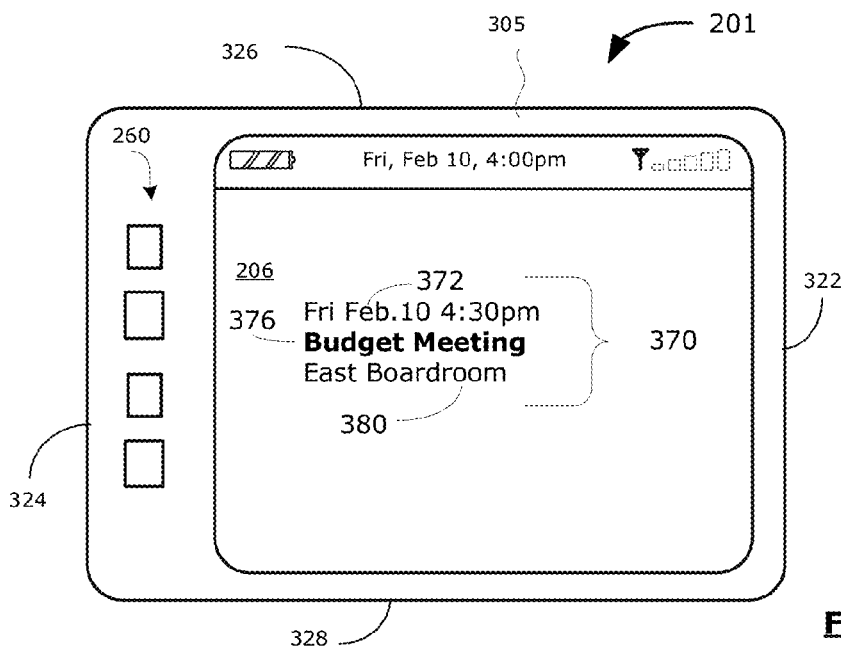
FIG. 3 is a front view of the mobile communication device in a landscape orientation.

In some example embodiments, hard control buttons or keys 260, represented individually by references 260a, 260b, 260c, 260d are located on the case 304 of the device 201 to generate corresponding input signals when activated. In some example embodiments, some or all of keys 260 may be replaced soft keys implemented on display 210. In some example embodiments the device 201 can be moved between portrait and landscape orientation modes, as seen in FIGS. 2 and 3 respectively. The device 201 may be configured, based on inputs from an orientation sensor 251 such as an accelerometer in orientation subsystem 249, to automatically detect its orientation and change the orientation of information displayed on display screen 206 between landscape and portrait in response thereto.

In an example embodiment, the notification module 226 is configured to present notification messages on the display screen 206. The notification messages can be associated with various external trigger events—for example, the receipt of a new email message, text message, instant message, phone call or voice mail message at the device 201 can each result in an associated notification message that can be displayed on the display screen 204 to provide information about the newly received message or phone call. In this regard, FIG. 2 illustrates an example of a notification message 370 generated by processor 240 in association with a new electronic message recently received at the device 201. In the example of FIG. 2, the notification message 370 includes a time field 372 indicating the time that the message was received at, a sender field 374 indicating a name or other identifier for the sending party, a message subject field 376 (in the case of an email message), and a content field 378. In some examples, a type field 373 may also be provided to indicate the type of message (for example: email=EM; text=T; instant messaging=IM; voice mail=VM). The content field 378 may include up to a predetermined number of characters from the original message content to allow a user to preview part of the message content. Upon viewing a notification message 370, a user has different options—for example, pressing a predetermined key such as key 260d may cause the entire message associated with the notification message 370 to be displayed; pressing a different predetermined key such as key 260c may cause a "compose reply" interface to be displayed to facilitate a reply to the message; and pressing yet a different predetermined key such as key 260b may cause the message notification 370 to be removed from the display screen 204.

In some example embodiments, notification messages can also be associated with internal trigger events such as a task or calendar reminder, or movement of the device 201 into or out of a predefined geographic area, among other things, and in this regard FIG. 3 illustrates an example of a further notification message 370 generated by processor 240 in association with a calendar reminder for an upcoming calendar event stored in a calendar data associated with the device 201. In the example of FIG. 3, the notification message 370 includes a time field 372 indicating the time of the calendar event, a meeting subject field 376, and a meeting location field 380. In some example embodiments various types of services that push data or messages to the device 201 could act as trigger events that would cause the processor 240 to generate a corresponding notification message. For example, messages from a social networking website such as messages regarding a change in status or posting of new information could act as trigger events, as could notification of new software updates available for download by the mobile device 20.

Figure 4:
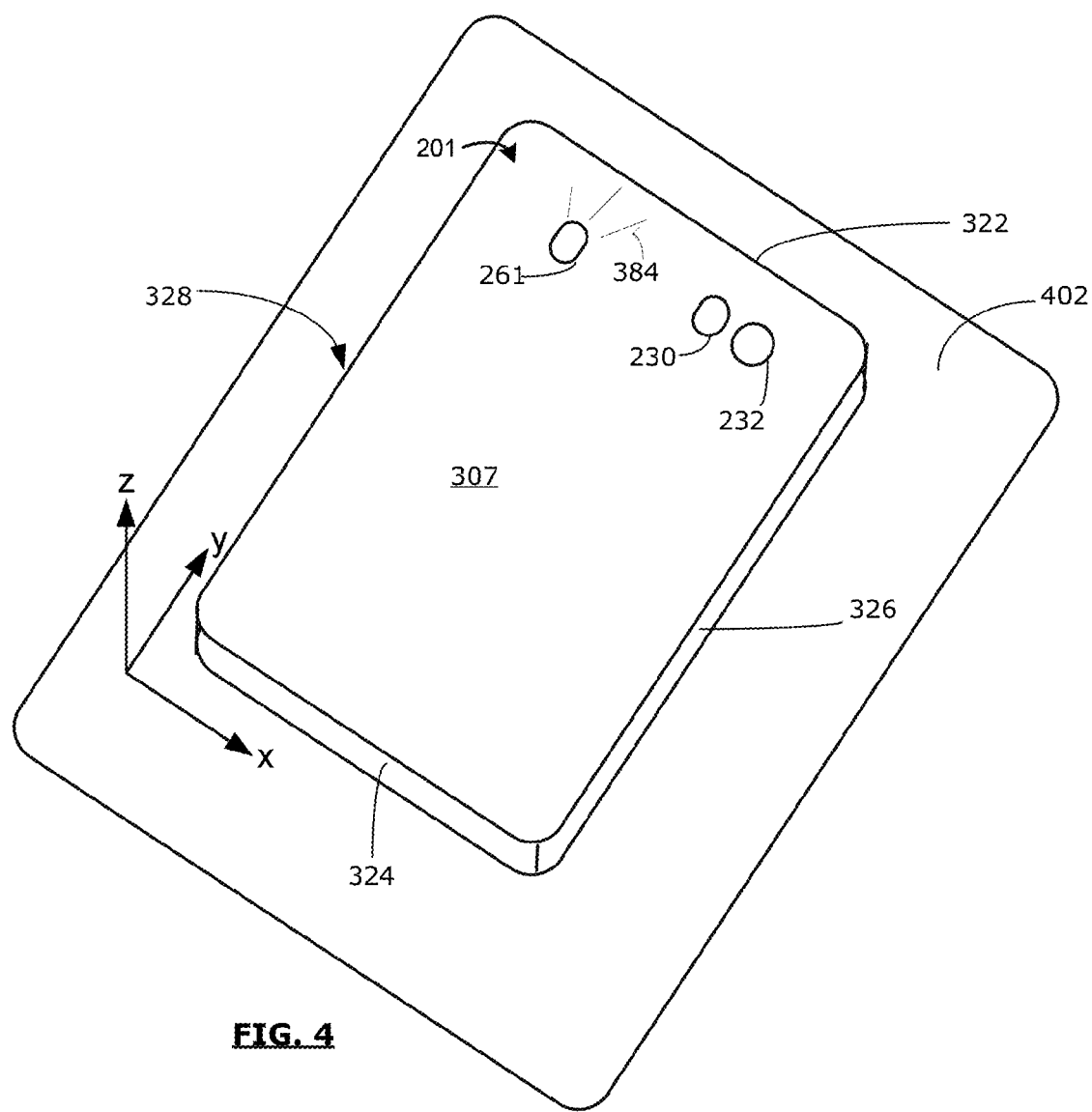
FIG. 4 is a perspective view of the mobile communication device resting face down on a support surface.
Figure 5:
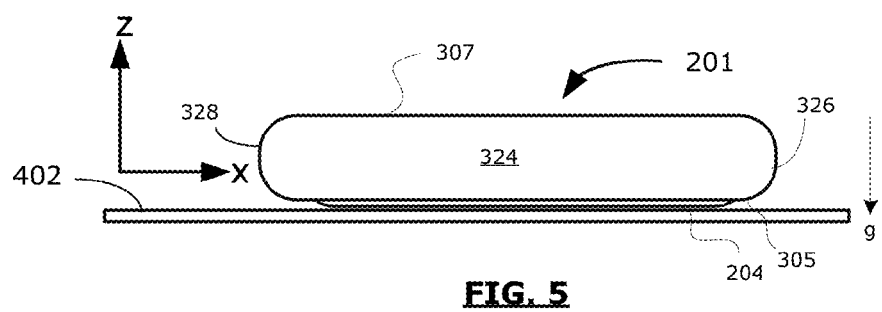
FIG. 5 is a side view of the mobile communication device resting on the surface.

As indicated above, in example embodiments, the notification module 226 is configured to present information about notification messages 370 differently, depending on a sensed orientation of the electronic device 201, to enhance privacy of the user of the device. In this regard an example embodiment of a tilt-activated notification message display process 2400 will now be explained with reference to the flow diagram of FIG. 25 and FIGS. 4-15. In the described example, a new email message has arrived at device 201 resulting in information for a notification message 370 similar to that shown in FIG. 2. FIG. 4 shows a perspective view of mobile device 201 in an initial, stationary, face down position resting on a generally planar horizontal support surface 402 with its generally planar display screen 204 facing downwards. In FIG. 4, support surface 402 represents the surface of a table or desk or podium for example. In the Cartesian coordinate system shown in FIG. 4, the X and Y axes extend in horizontal directions and the Z axis extends in a vertical direction. FIG. 5 shows a side-view of the device 201 in the same facedown position as FIG. 4. FIGS. 4 and 5 represent how a user may place his or her device 201 when sitting in a meeting or at a desk or standing near a flat support surface. The face down display screen 204 cannot be viewed, and accordingly any information on the display screen 204 is private. In the Figures, arrow "g" indicates the direction of gravitational force.

As indicated in Action 2402, in an example embodiment the processor 240 is configured to monitor for a notification message trigger (for example a new message, or phone call, or a calendar or task reminder) and sense when the device 201 is in a stationary face down position as shown in FIGS. 4 and 5. In at least one example embodiment, orientation sensing is based on inputs received from a position sensor such as an accelerometer 251 or gyroscope. In some embodiments, other position sensing elements could be used to assist in determining device orientation, including for example inputs from camera sensor 232. In some embodiments, the camera sensor 232 (or other light sensor) could be used to determine if the device is in a face down or face up position—for example, if a camera sensor 232 on the front face of the device detects very little ambient light, such information can be an indicator the device is face down on an opaque surface, and if a camera sensor 232 on the front face of the device detects a higher level of ambient light such information can be an indicator the device is face up. Similarly, the device 201 may be configured to adjust a backlighting or display brightness of the display screen 204 in response to a level ambient lighting sensed by a sensor—such a feature can improve privacy as lower lighting levels can be used in darker environments to display notices on the display screen.

In some embodiments when the device 201 is in a face down stationary position for a predetermined length of time the device 201 enters a power saving mode in which the display screen 204 either goes blank or displays a default screen. As indicated in Action 2404, if a new notification message trigger event occurs when the device 201 is oriented display screen down and stationary, the processor 240 causes a new notification message indicator to be generated—for example, a visual indication (indicated by lines 384 in FIG. 4) can be provided to a user of the device by a flashing LED 261 located on a visible surface of the device such as the side edges or upward facing back 307. In some example embodiments, one or both of the flash rate or color of the LED 261 could be used to indicate the type of event for which the notification message is being generated, for example a new e-mail message, a new text message, a new instant message, a calendar reminder, a task reminder or a new voice mail message. The flash rate or color or both of the LED 261 could also be used to indicate the number of un-viewed or new notification messages waiting to be viewed. In some examples, the device 201 may alternatively, or also, provide a physical indication in the form of a vibration or an aural indication in the form of a sound indicating that a new notification message is available to the user of the device 201. In some examples, the flash 230 associated with device camera sensor 232 could be controlled to provide a new notification message indication. In some example embodiments, the display screen could be configured so that some light leaks even when the display screen is face down, and the display screen flashed repeatedly (for example, all red) for a predetermined duration to visually provide a new notification message indication.

In at least some example embodiments, the new notification message indicator generated in Action 2404 can be perceived by various people in the proximity of the device 201, however the new notification message indicator provides little or no details about the content or character of the notification message. In some example the device 201 can be configured to suppress the new notification message indicator so that information that a new notification message is waiting to be viewed can be hidden.

Figure 6:
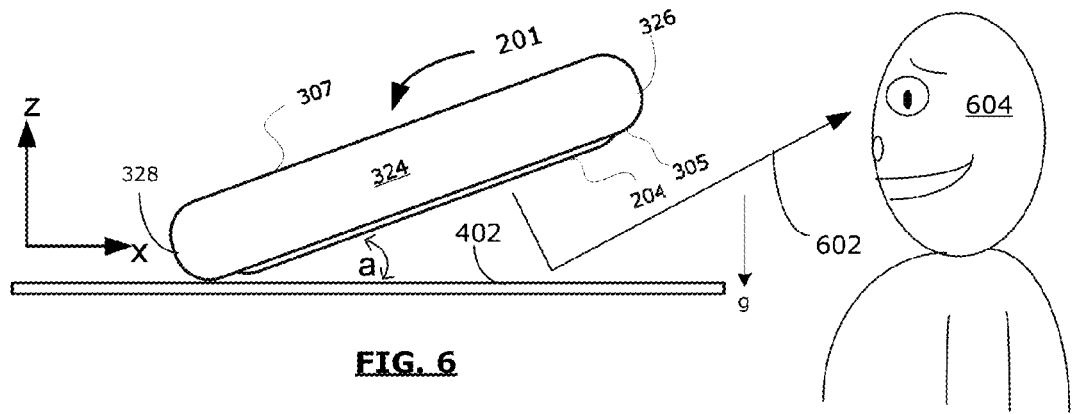
FIG. 6 is a side view of the mobile communication device tilted a first angle with respect to the surface.
Figure 7:
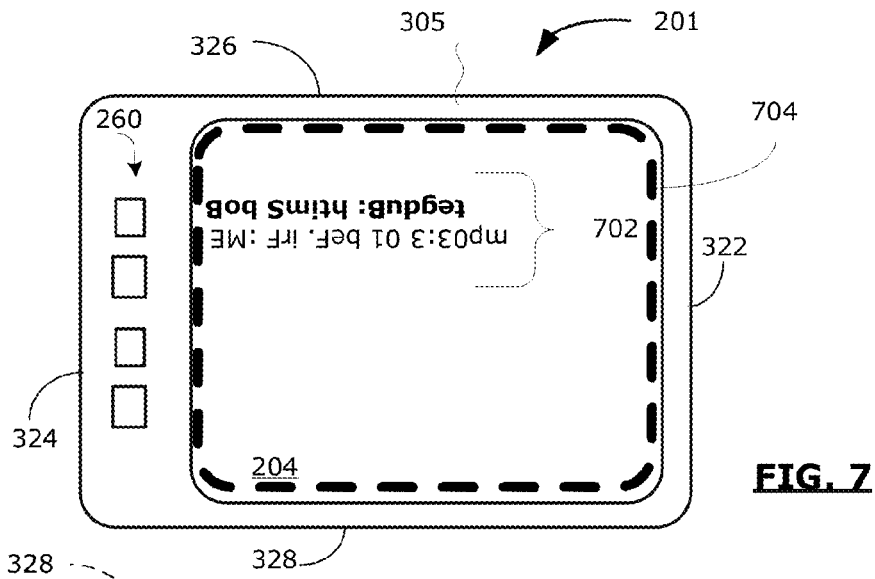
FIG. 7 is a front view of the mobile communication device showing an image presented on the device when it is in the orientation of FIG. 6.
Figure 8:
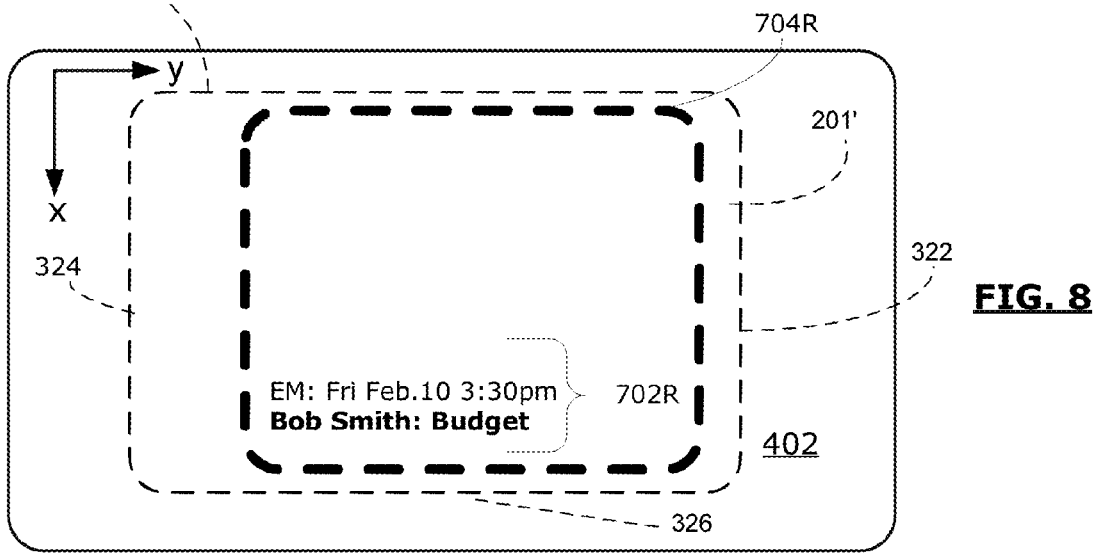
FIG. 8 is a plan view of a reflective surface reflecting the image displayed on the mobile communication device of FIG. 7.

As indicated in Action 2406, once a new notification message is waiting to be viewed, the processor 240 monitors the face down device 201 to determine if the device 201 is tilted to a first orientation that exceeds a threshold angle "a" from its stationary, face down position. In particular, referring to the embodiment of FIG. 6, the processor 240 is effectively monitoring to see if a device user 604 tilts the device upwards on the support surface 402. More specifically, based on input from orientation subsystem 249, the processor 240 detects when the device 201 is tilted at least "a" degrees relative to a horizontal plane, that is, the angle between the display screen 204 and the horizontal surface in this example. In FIG. 6, the tilt axis is parallel to the horizontal plane that runs into the paper along the Y axis, and is generally parallel to the device side edge 328 and the planar display screen 204—thus the processor 204 monitors to determine if the edge of the device 201 that is closest to a device user 604 (edge 326 in FIG. 6) is being tilted up while the edge of the device furthest from the user (edge 328 in FIG. 6) remains substantially resting on the support surface 402. Once the threshold tilt angle "a" is reached, the processor 240 causes selected information 702 from the notification message 370 to be displayed in a first notification message display mode on the display screen as shown in FIG. 7 (Action 2408). In the example embodiment, the displayed information 702 is displayed so that it can be viewed as a reflection off of the support surface 402—arrow 602 illustrates the path of light from the display screen 204, reflected of surface 402, as viewed by device user 604. FIG. 8 is a plan view showing the reflected image 702R projected onto the surface 402-dashed line 201' represents the footprint of the device 201 over the surface 402, which effectively blocks the reflected image 702R from potential viewers who are not positioned in the location of device user 602, thus preserving the privacy of the displayed information 702.

In order to allow the device user 604 to comprehend the reflected image 70R, the displayed information 702 is presented on the display screen 204 as an inverted mirror image a shown in FIG. 7. In particular, each character is inverted, i.e. rotated 180 degrees from how it would normally be presented, and the vertical ordering of the displayed lines of text reversed so that the lowest line becomes the top line. In the example of FIGS. 6-7, the displayed information 702 only includes selected fields from the notification message 370, notably the sender field, subject field and time field—the content field is omitted. In different embodiments, more or less information or fields from the notification message 370 could be included in the displayed information 702, and in some examples the amount of displayed information could be user configurable.

In FIGS. 6-8, the displayed information 702 is positioned on display screen 204 closer to the raised edge 326 than the pivot edge 328 of the device 201, in recognition of the fact that at lower pivot angles it will be easier for the device user 604 to see reflections located closer to the higher raised edge 326 of the device 201.

Accordingly, it will be appreciated that by tilting the closest edge of device 201 upwards a minimum of "a" degrees, the device user 604 can discretely view reflected image 702R with the reflection being substantially blocked from other peoples' view by the device 201. In an example embodiment, in addition to displaying information 702, the processor 240 also causes a region 704 (see FIG. 7) of the display screen to be lit up as the device 201 is tilted, resulting in a reflected image 704R on surface 402(see FIG. 8). In some embodiments, the illuminated region 704 is either color coded or flash coded or both to provide some information about the notification message—for example flashing red to indicate a new email message, solid red for a text message, blue for calendar reminder, etc. In some embodiments, the border region 704 is displayed as soon as the device 201 begins to get tilted and turns off once the angle "a" or some other threshold angle is reached.

In some example embodiments the displayed information may be scrolled across the display screen 204 to increase the amount of information presented, or the size of the characters adjusted for enhanced readability. In some embodiments the scrolling speed can be controlled by pivoting the device 201 back and forth within a range of the threshold angle for the current display mode. For example, tilting back down could slow the scroll speed and tilting back up could increase the scroll speed. In various embodiments, the displayed information may scroll while the device is moved within a range of the threshold angle and stop scrolling when the device is held at stationary tilt angle, thus permitting the user to scroll the displayed information by tilting the device and freeze the displayed information by maintaining the device at a stable tilt angle.

As indicated in Actions 2410, 2418 and 2424, throughout the process 2400 the processor 240 monitors to determine if the device 201 is tilted back down into is starting display screen face down position of FIG. 5, and if the device 201 is returned to its face-down position, the new notification message indicator 2412 is turned off and the displayed notification information removed from the display screen (action 2412). In some example embodiments, when a new electronic message arrives at the device, in addition to new notification message indicator 384 a new message marker is also displayed on a status bar portion of the device screen. By way of example, FIG. 2 shows a new message marker 380 in the form of a "splat" (shown as a star) over a mail indicator displayed in the status bar region of the display screen 204. In some example embodiments, the new message marker 380 remains active until the associated message is actually viewed, regardless of whether information from the notification message associated with the new message is viewed by tilting the device. For example—a quick tilt of the device 201 could be used to turn off the new notification message indicator 384 (with or without the message 702 actually getting viewed) but the new message marker 380 associated with the message could remain active.

Turning again to process 2400, if the device 201 is tilted further from the first orientation to a second orientation beyond a second threshold angle "b", the displayed information 702 is modified and displayed in a second display mode (Actions 2414, 2416). In particular, in the illustrated embodiment, the displayed information 702 in FIGS. 9-11 at tilt angle "b" is the same as displayed as it was at the smaller tilt angle "a", however the positioning of the displayed information 702 has shifted down to a position on the display screen 204 that is closer to the pivot edge 328 of the device 201 rather than the raised edge 326. Such a feature recognizes that the further the displayed information is from the surface 402 the weaker the reflected image 702A—hence shifting the displayed information 702 as the tilt angle increases keeps the image close to the surface 402, improving the reflected image 702R. The displayed information 702 could be shifted in one discrete step as the angle "b" was reached, or alternatively the displayed information 702 be incrementally stepped or continuously "slid" or scrolled down or up the screen as an animation between the positions shown in FIGS. 7 and 10, as the user tilted the device further up or down, and the image could be maintained in a constant position when the device was maintained at a constant tilt angle.

In an example embodiment if the device 201 is tilted to yet a third orientation that is greater than a further threshold tilt angle "c" the displayed notification message information is modified again and displayed in a third display mode (Actions 2420 and 2422). In particular, referring to FIGS. 12 and 13 (which show side and front views of the device 201 at tilt angle "c"), selected notification message information 710 is displayed on the display screen 204 in a manner to facilitate direct viewing by the device user 604, as shown by light path 606, at a small direct viewing angle "v" relative to the display screen. In this regard, the displayed notification message information 710 (which can be less, the same as, or more than the information included in displayed information 702) is displayed as having a distorted or perception corrected or perception modified font compared to the default display font used by the device 201. In particular, the displayed information 710 can be displayed with vertically stretched text having a text height H to text width W aspect ratio that is substantially larger than the default font. Additionally, the aspect ratio may vary from the top of the text to the bottom, such that the text width W(B) at the bottom of the displayed text is wider than the text width W(T) at the top of the displayed text, providing a keystone effect that allows the text to be read at small viewing angle "v". In example embodiments, the displayed information 710 can scroll across the display screen 204, and the rate of scrolling described in the manner described above by adjusting the tilt angle within a range about angle "c". In some example embodiments, the aspect ratio of the displayed information 710 is adaptively adjusted as the tilt angle changes within a range of angle "c" to accommodate different viewing angles "v".

In an example embodiment if the device 201 is tilted to yet a fourth orientation beyond a further threshold tilt angle "d" the displayed notification message information is modified again and displayed in a forth display mode (Actions 2426 and 2428). In particular, referring to FIGS. 14 and 15 (which show side and front views of the device 201 at tilt angle "d"), angle "d" represents a standard direct viewing angle for the device 604, and all fields of the notification message 370 are displayed in default font size on the display screen 204. In some example embodiments, when the notification message is associated with a new electronic message, rather than showing just a message preview, tilting to the fourth orientation causes the entire electronic message to be shown on the display screen within a message viewing user interface function of a messaging application on the device 301 and the message is then tracked by the device as being "read".

It will thus be appreciated that the notification message viewing process described above allows a device user to discretely view notification messages and progress through a series of viewing modes that are dependent on the device tilt angle in order to control the manner and amount of information displayed by the device 201. The pivot edge is shown as right side edge 328 in FIGS. 6-15, with the device 201 taking a landscape orientation. In example embodiments, the processor 240 is configured to detect which of the four side edges 322, 324, 326 or 328 is used as the pivot edge and display the notification information accordingly. In alternative embodiments, the processor 240 is configured to only accept one edge (for example bottom side edge 324), providing further possible privacy as the information will only be displayed when tilting occurs on the designated tilt edge. In some embodiments, which edges can be designated as acceptable tilt edges is user configurable.

In some embodiments, when multiple notification messages are waiting to be viewed, returning the device 201 to the face down position subsequently tilting the device back up brings up the next notification message for viewing. In some examples, the display modes are reversible such that tilting the device back down switches through the display modes in the reverse order. In some embodiments, the device 201 is configured to accept other or alternative user inputs (in addition to device tilting) to advance through the various notification message display modes—for example, a verbal command, a touch screen tap, or user activation of one or more of the control keys 260 (one or more of which could be located on a side edge of the device such as volume keys) could be used to switch between the display modes such as those shown in FIGS. 8, 11, 13 and 15. In some example embodiments, a motion or orientation sensor such as the accelerometer 251 of the device could be used to detect a "tap" by a user's finger on the back of the device 201, and the device 201 be configured to advance to a next display mode on detecting a tap input.

In some example embodiments, in addition to displaying a new message notification identifier 384 and a new message marker 380, the device 201 also marks messages as "read" and "unread" in a message list generated by a message viewing application resident on the device. For example an unread message may be identified by an open envelope icon or bold text or both. In example, embodiments, the new message notification identifier 384, new message marker 390 and "read"/"unread" marker can each be individually controlled based on the tilt angle of the device 201 and the duration the device remains at such tilt angles. For example, as indicated above, tilting of the device 201 away from its stationary face down position for even a moment could cause the new message notification identifier 384 to disappear without affecting the message marker 390 and "read"/"unread" marker, and tilting of the device for a threshold period to a threshold orientation could cause the new message marker 390 to be removed without affecting the "read"/"unread" marker, and tilting yet further distance for a threshold period cause the "read" marker to be activated.

In some example embodiments, the reflective viewing modes shown in FIGS. 6-11 could be used to discretely view information other than notification message information on the display screen—for example, tilting of the device in the could cause a clock image showing the current time to be projected onto the support surface so the reflected clock image can be viewed in correct orientation. In some example embodiments the reflected clock image could be displayed when the device is tilted and there is no pending new message notification to display.

In an example embodiment the angles "a", "b" and "c" are 70 degrees or less, and angle "d" 90 degrees or less—by way of non limiting example, angle "a" could be between 1 and 5 degrees; angle "b" between 10 and 20 degrees greater than angle "a"; angle "c" between 10 and 30 degrees greater than angle "b"; and angle "d" between 20 and 40 degrees greater than angle "c". In some example embodiments, the threshold angles have can be user configured to vary from preset default values. In some example embodiments the starting position of the device may not be completely horizontal—for example the device 201 could be face down on an angled podium. The threshold angles could in some embodiments be determined relative to the starting position or relative to a absolute horizontal plane or a combination thereof. In some embodiments, if the device is resting for a predetermined duration (for example a minute), the resting position could be used as a base-line position from which angles a, b, c and d are calculated and measured.

In some example embodiments, the amount of information displayed in each of the display modes can be dependent on whether or not the device is locked. In some embodiments, the tilt display modes may be disabled or alternatively fully active when the device is locked. However, in some embodiments when the device is locked the information shown in each of the display modes could be a sub-set of the information displayed when the device is unlocked. For example, sender name could be shown without subject or content information.

As will be appreciated from the present description, the displayed information can be modified in different ways between the different viewing modes—for example, the content of the information displayed on the device screen, the position of the displayed information on the device screen, the orientation of the displayed information on the device screen, a scroll speed of the displayed information, a size of the displayed information, a font of the displayed information, an aspect ratio of the displayed information, and a color of the displayed information are features that can be modified. In some example embodiments a distinct message can be displayed in each viewing mode (for example, viewer name on its own in one mode, subject on its own in another mode). Furthermore, the angles and device orientations associated with the modes, and the number of modes can be varied in different embodiments, some non-limiting examples of which will be provided below.

Figure 16:
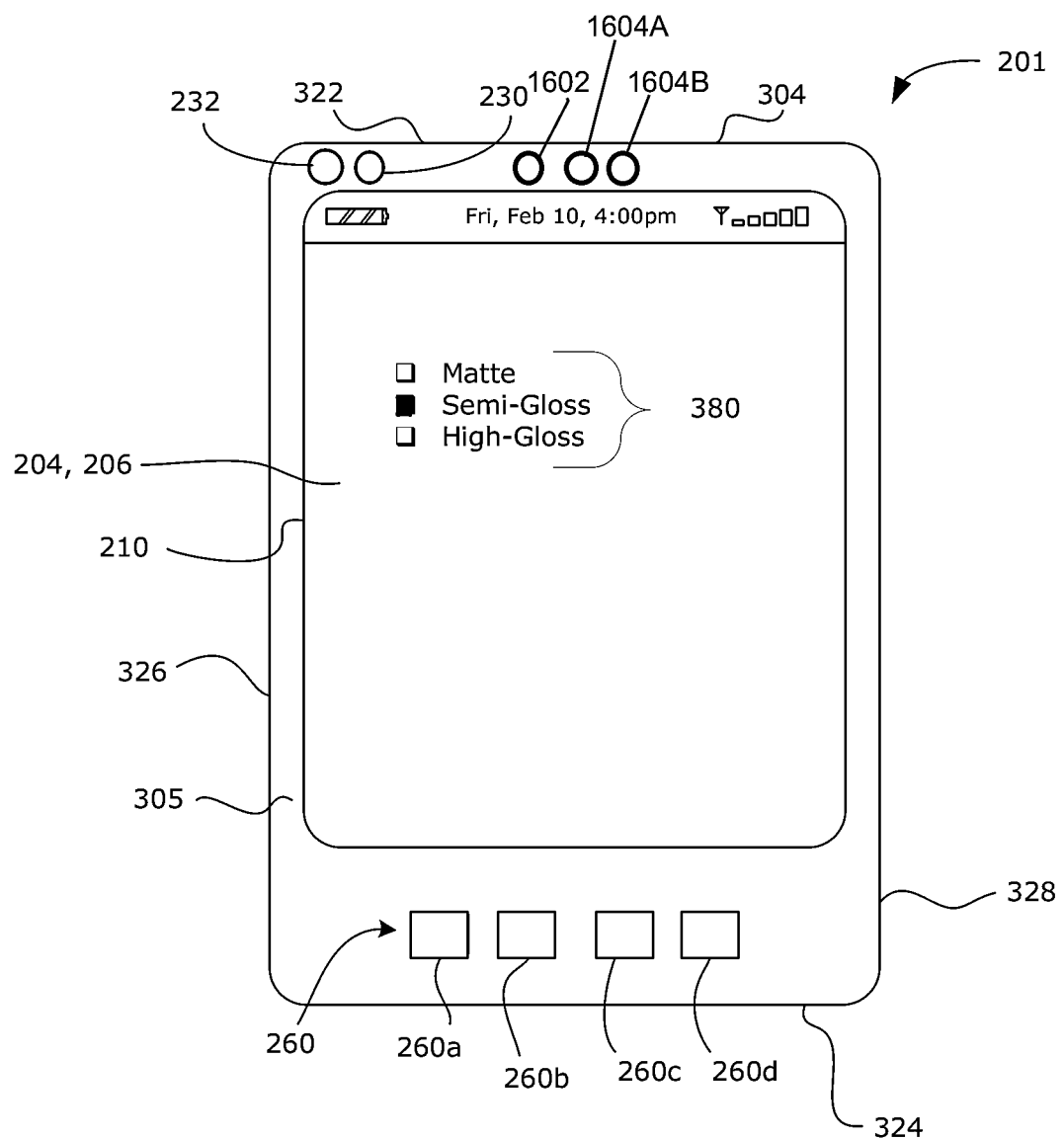
FIG. 16 is a front view of the mobile communication device showing a sample surface selection interface.

The tilt display modes described above may not be appropriate for all support surfaces 402—for example, the reflective modes may not work on matte surfaces, and high gloss surfaces may allow more information to be reflected at lower angles than semi-gloss surfaces. In some example embodiments, the processor 240 can be configured to change one or more of the threshold angles and the display modes associated with the threshold angles in dependence on the texture of surface 402. In some embodiments, the type of surface texture is provided by the device user, and in this regard FIG. 16 illustrates a menu screen 380 that allows a user to configure the device 201 for a matte surface, semi-gloss surface or high gloss surface. In some embodiments, the device 201 may include a light based surface reflectance estimation system that includes a light based sensor on the front face 304 such as a forward facing camera sensor 232 that can be used to provide information for the processor 240 to automatically make a surface texture determination as the device 201 is laying in a face-down position. In some example embodiments, as the device 201 is first tilted upwards a calibration pattern is projected by the screen 204 onto the surface 402 and measured by the camera sensor 232 provide a surface texture reference value that can be used by the processor 204 to adaptively determine which tilt viewing modes, viewing mode characteristics and associated threshold angles are appropriate for the surface 402.

In one example embodiment the display modes described above are used when the surface texture corresponds to semi-gloss (which could be a user input surface selection, or automatically determined or estimated based on light sensor input). In the case of a matte surface, the number of display modes could be reduced to two, for example the perception corrected text display mode of FIGS. 12 and 13 and the full message display mode of FIGS. 14 and 15, as the reflective display modes would not be useful. In the case of a high gloss surface, the entire notification message could be displayed in the reflective display modes, with a shift directly to the full notification message direct view mode of FIGS. 14 and 15.

Figure 13:
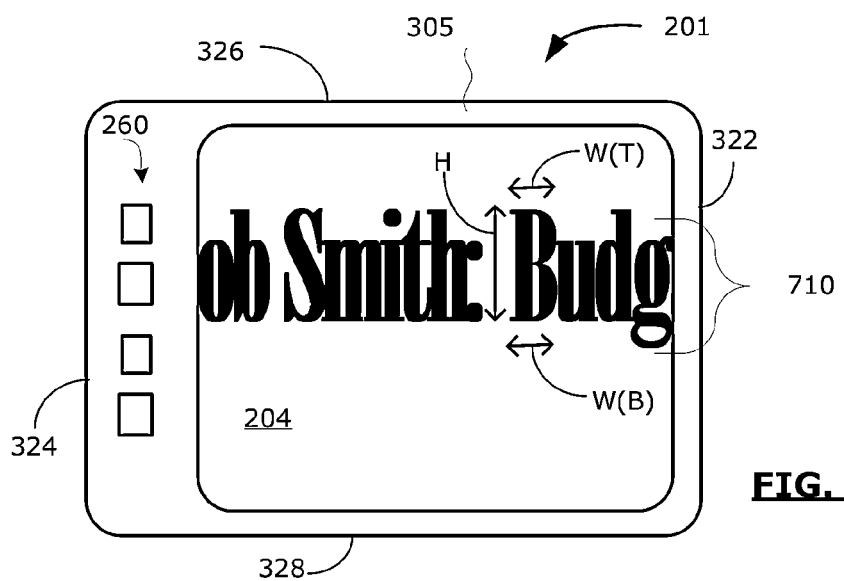
FIG. 13 is a front view of the mobile communication device showing an image presented on the device when it is in the orientation of FIG. 12.
Figure 14:
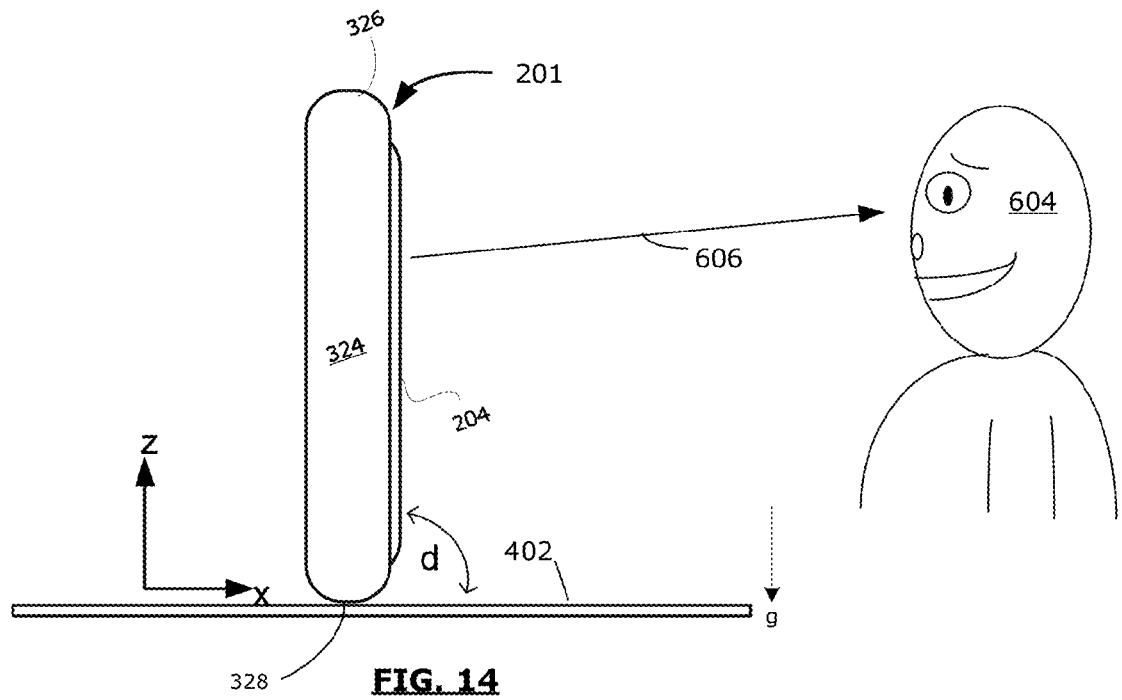
FIG. 14 is a side view of the mobile communication device tilted a fourth angle with respect to the surface.
Figure 15:
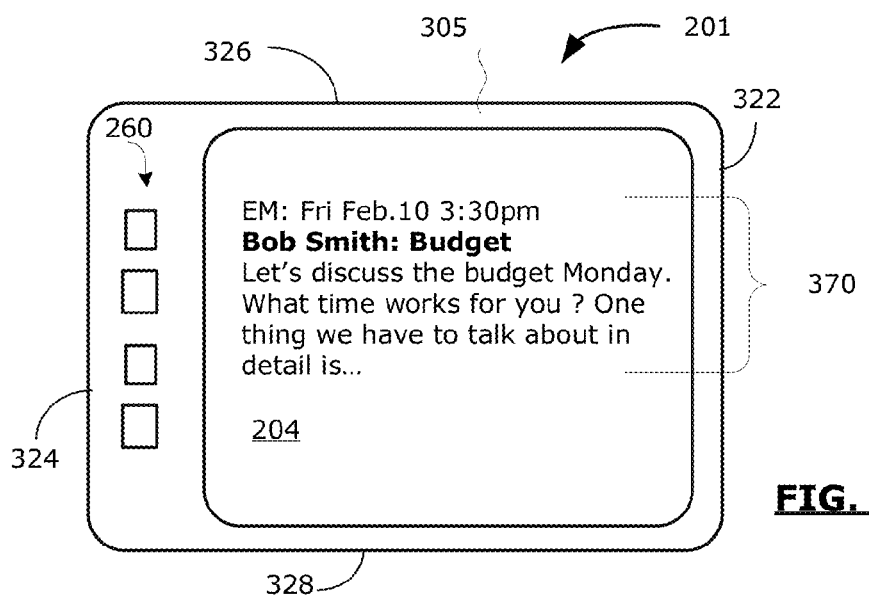
FIG. 15 is a front view of the mobile communication device showing an image presented on the device when it is in the orientation of FIG. 14.
Figure 26:
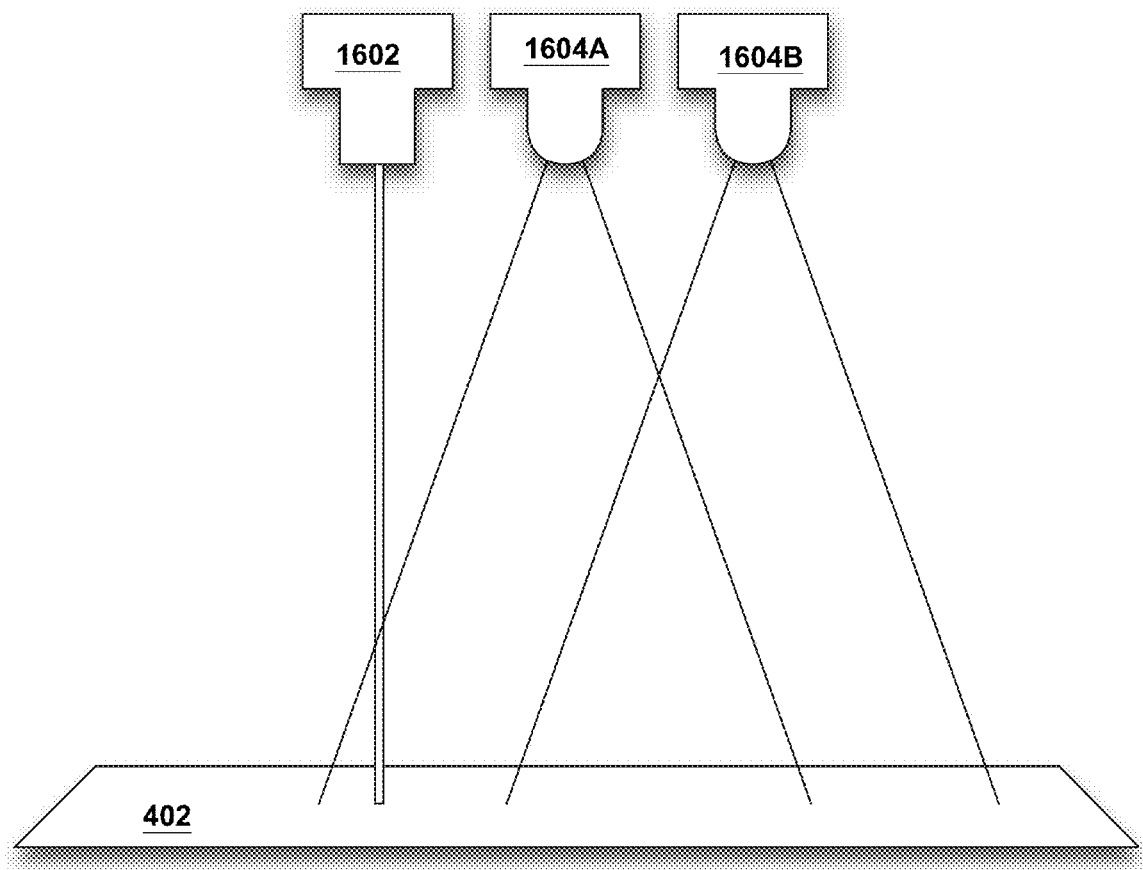
FIG. 26 illustrates an IR emitter and sensors of an example embodiment of the device.

As indicated above, the device 201 can be configured to include a surface reflection estimation system to provide information for the processor 240 to automatically make a surface texture determination as the device 201 is moved from a face-down position. In the system described above, the display screen or a forward facing camera flash function as a light based emitter and the camera sensor 232 as a light based sensor. In other example embodiments the emitter/sensor combination could use non-visible light. By way of example, as shown in FIG. 16, the surface detection system could include one or more IR (infrared) emitters 1602 (which could for example comprise one or more IR LEDs (light emitting diodes) and two or more spaced-apart IR sensors (which could for example include one or more photodiodes) 1604A, 1604B on its front face. After a notification message trigger occurs, if the orientation subsystem 249 indicates that the face down device 201 begins to moves from a face down position as shown in FIG. 5, the IR emitter 1602 is activated so that it projects a very narrow field of light (for example, a narrow laser pointer style beam) towards the surface 402 on which the device lies. The IR sensors 1604A, 1604B positioned next to the emitter 1602 then monitor for reflected IR light from the surface 402 as illustrated in FIG. 26. A reflective surface will tend to provide a tight, specular reflection of the IR light, whereas a less-reflective surface will provide a diffuse reflection. Accordingly, a comparison of the IR reflection detected by the two sensors 1604A and 1604B can be used to determine the size/intensity of the reflected light, from which the reflectivity of the surface 402 can be estimated. If the sensors 1604A and 1604B "see" a small, high intensity reflected dot, the reflection from the surface 402 is specular. If the dot is larger and more blurry, the reflection from the surface 402 is diffuse. If the dot is in between small and large, the surface is "semi-reflective". The device 102 can be preloaded with comparison thresholds for the sensors 1604A and 1604B to classify a surface as reflective, semi-reflective or matte, or in some embodiments a user can configure the device by taking readings from reference surfaces during a calibration routine As noted above, the surface reflectivity determination can then be used by the processor 240 to automatically select an appropriate rendering mode depending on the surface, for the device tilt angle. For example: on reflective surfaces, render the mirror image of the notification message so the user can read it in the reflection, as shown in FIGS. 7,8; on semi-reflective surfaces, render the mirror image of the notification message in a larger font so the user can read it in the reflection (animated as a ticker if the message notification requires more than one screen) (for example, an inverted image of what is shown in FIG. 13); on matte surfaces, render the notification so it can be read on the screen (possibly using asymmetrical projection) as shown in FIG. 13. In an example embodiment, two light sensors 1604A and 1604B (with simple lens assemblies) can be used for every light emitter 1602(IR or Laser) to determine the specularity of the surface 402. Each light sensor measures the light intensity of an area that slightly overlaps with the area covered by the other light sensor. This means that the specularity of the surface that reflects the light can be estimated by comparing the light intensity value measured by the two sensors (a more specular reflection will generate a larger difference between the two values). These same IR sensors and emitters can be used for proximity detection and in-pocket detection. In some example embodiments, the device may be limited to a single IR sensor for estimating surface reflectivity.

In some example embodiments, additional information from the device orientation subsystem 249, including information from an orientation sensor such as accelerometer 251, can be used to further refine the processing done by the surface reflection estimation system. By way of example, information from the accelerometer 251 can be used to estimate the relative location of the device 201 to the surface 402 (for example, the distance between the IR sensors and the surface) and this location information combined with the readings from one or more of IR sensors 1604A and 1604B to estimate the surface reflectivity. In particular, changes in acceleration, proximity and orientation detected by the orientation subsystem 249 may be interpreted by the portable electronic device 100 as motion of the portable electronic device 100.

When the changes in acceleration, proximity and orientation are within threshold tolerance(s) of regularity or predictability, the changes in acceleration, proximity and orientation match predetermined motion criteria (e.g., which may for example be stored in the memory 244) and the changes may be interpreted by the portable electronic device 201 as indicating movement of the device 201 from a position where it faces a surface 402, such as shown in FIG. 5, to a further position such as shown in FIG. 6 where the device screen 204 is located at angle a relative to the surface 402. In an example embodiment, such information is used to estimate the location (including distance and angular position) of IR sensors 1604A, 1604B and IR sensor 1602 relative to the surface 402, which may can then be correlated with the light information read by sensors 1604A and 1604B to estimate the reflectance index of the surface 402. By way of example, a look up table could be stored in device memory 244 or 248 in which estimated reflectances are mapped to a combination of relative location information as measured by the orientation subsystem and reflected light information as measured by sensors 1604A and 1604B. In some examples, equations could be used to determine the estimated reflectance index in dependence on the location information and the sensed reflectance information. In some embodiments, the device 201 could be calibrated by instructing a user to take reference reflectance readings from surfaces at different relative positions and distances.

Figure 27C:
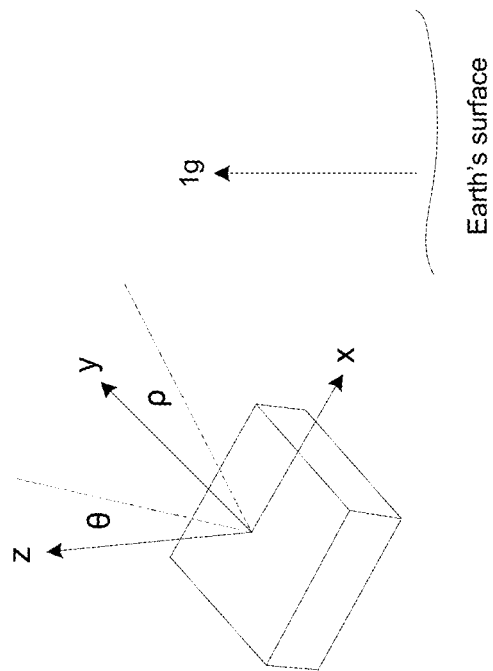
FIGS. 27A to 27C are schematic diagrams illustrating the assignment of pitch and roll vectors of a three-axis accelerometer in accordance with one example embodiment of the present disclosure.
Figure 27B:
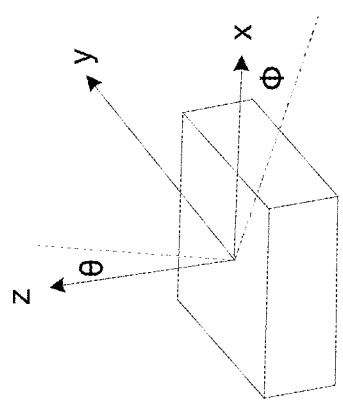
Figure 27A:
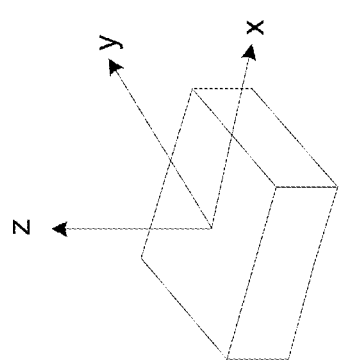

Referring now to FIGS. 27A to 27C, the assignment of relative location information in the form of pitch and roll vectors of three-axis accelerometer 251 in accordance with an example embodiment of the present disclosure will be described. The accelerometer 251 has three mutually orthogonal sensing axes denoted "x", "y" and "z". The x-axis and y-axis are aligned with a horizontal plane defined with respect to the face or display screen surface of the portable electronic device 201. The z-axis is perpendicular to the horizontal plane of the portable electronic device 201. The z-axis will detect when portable electronic device 201 is moved vertically from a face-down position.

Figure 28A:
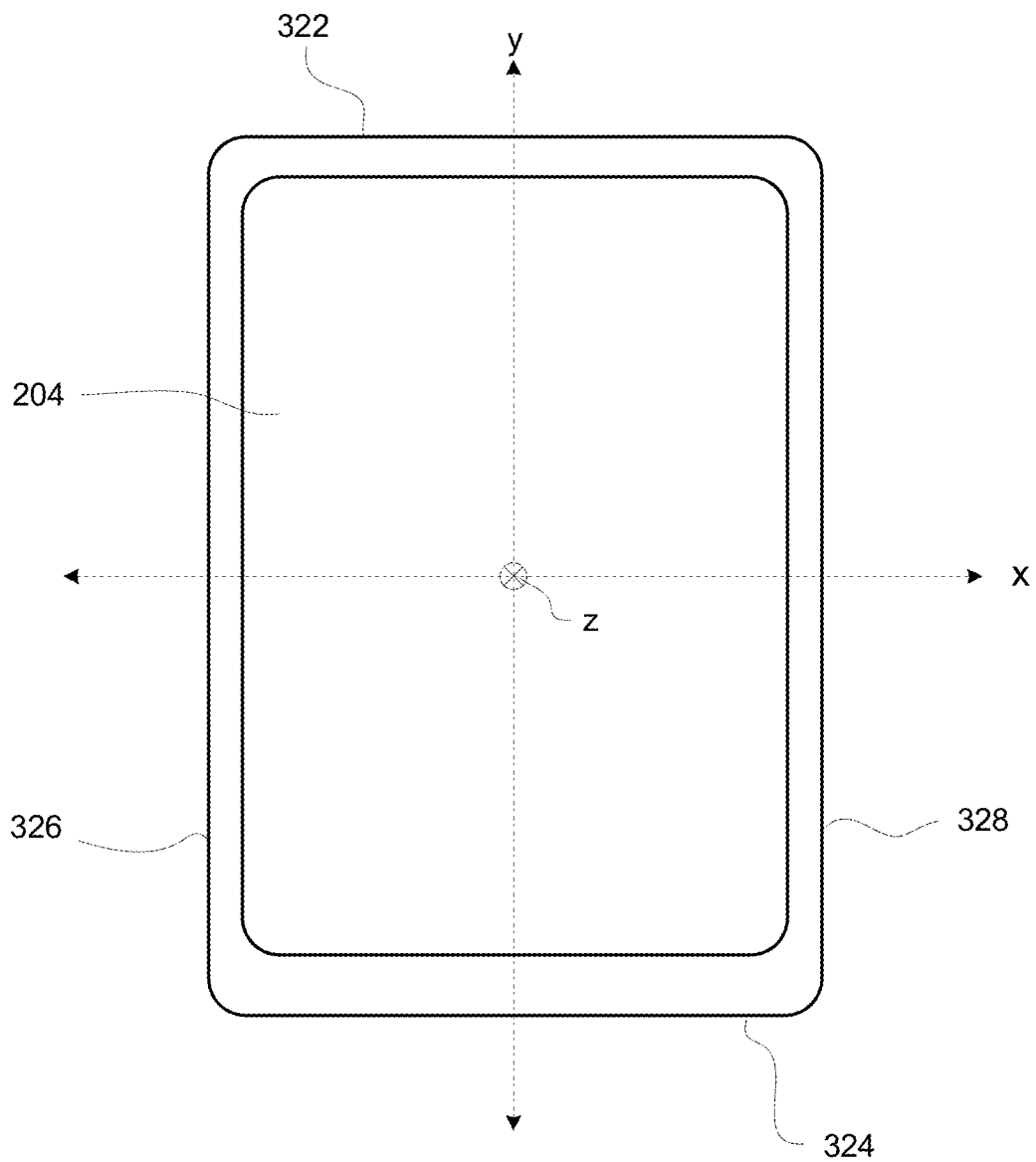
FIG. 28A is a front view of a portable electronic device showing sensing axes of three-axis accelerometer in accordance with one embodiment of the present disclosure.
Figure 28B:
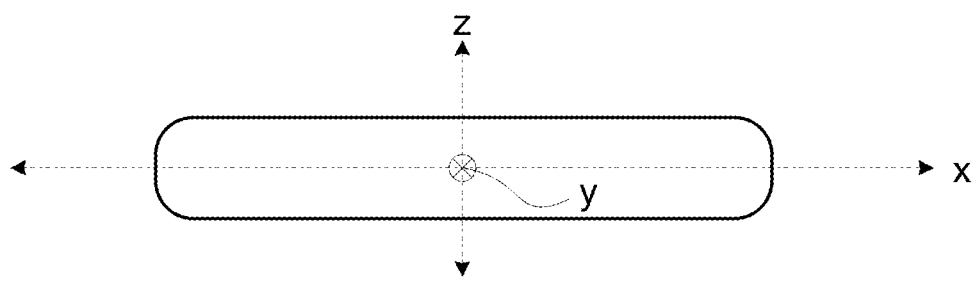
FIG. 28B is a top view of the portable electronic device of FIG. 28A.

Referring to FIGS. 28A and 28B, the alignment of the "x", "y" and "z" axes of the accelerometer 251 with axes of the portable electronic device 201 in accordance with one embodiment of the present disclosure is shown. The x-axis is aligned about an axis extending laterally along the midpoint of the portable electronic device 201 between the top 522 and bottom 524 ends respectively. The y-axis is aligned about an axis extending longitudinally along the midpoint of the portable electronic device 201 between the left 526 and right 528 sides respectively. The z-axis extends perpendicularly through the x-y plane defined by the x and y axes at the intersection (origin) of these axes. It is contemplated that the "x", "y" and "z" axes may be aligned with different features of the portable electronic device 201 in other embodiments.

As shown in FIG. 27A, if the portable electronic device 201 is positioned horizontal (level with the ground), the z-axis measures 1 g in the z-axis. When the portable electronic device 100 is tilted away from the horizontal, the z-axis baseline reading is moved downwards away from 1 g level. As shown in FIG. 27B, pitch ($\phi$) is the angle of the x-axis relative to the ground. $\theta$ is the angle of the z-axis relative to gravity. As shown in FIG. 27C, roll ($\rho$) is the angle of the y-axis relative to the ground. It will be appreciated that rotation may occur about any combination of sensing axes. The concepts and methodology described herein can be applied to any orientation and any combination of pitch (φ), roll (ρ) angles, and θ (the angle of the z-axis relative to gravity). The pitch (φ), roll (ρ) and the angle (θ) of the z-axis relative to gravity may be determined, for example, using standard equations. For example pitch (φ), roll (ρ) and the angle (φ) of the z-axis relative to gravity may be calculated using the following equations:

$$\varphi = \arctan \frac{x_{accel}}{\sqrt{y_{accel}^2 + z_{accel}^2}}$$

$$\rho = \arctan \frac{y_{accel}}{\sqrt{x_{accel}^2 + z_{accel}^2}}$$

$$\theta = \arctan \frac{\sqrt{x_{accel}^2 + y_{accel}^2}}{z_{accel}}$$

where $x_{accel}$, $y_{accel}$ and $z_{accel}$ are measurements from the x, y and z-axes of the three-axis accelerometer. Pitch (φ), roll (ρ) and angle (θ) of the z-axis relative to gravity can also be calculated by other means.

Although surface 402 is described above as a horizontal surface, the surface 402 that the device 102 is facing or resting on could be a non-horizontal surface (for example an angled podium rest). Accordingly, in at least some example embodiments, the location of the device 201 is determined relative to an initial position in which the display screen is in a stationary location adjacent to and facing surface 402 and the initial position need not be a horizontal position. In some example embodiments the device 201 is configured to determine that the device is in an initial stationary position with its display screen resting against a surface by determining, after the motion is detected for a threshold time, if the light intensity measured by the IR sensors 1604A and 1604B is negligible or below a predetermined threshold both with the IR emitter 1602 activated and based on ambient IR readings without the IR emitter 1602 activated. In some example embodiments, in addition to using light intensity measurements, one or more of the pitch (φ), roll (ρ) and z-axis (θ) angles (θ) are compared against predefined ranges in order to determine that device 201 is in an initial resting position with its screen facing a surface.

Figure 9:
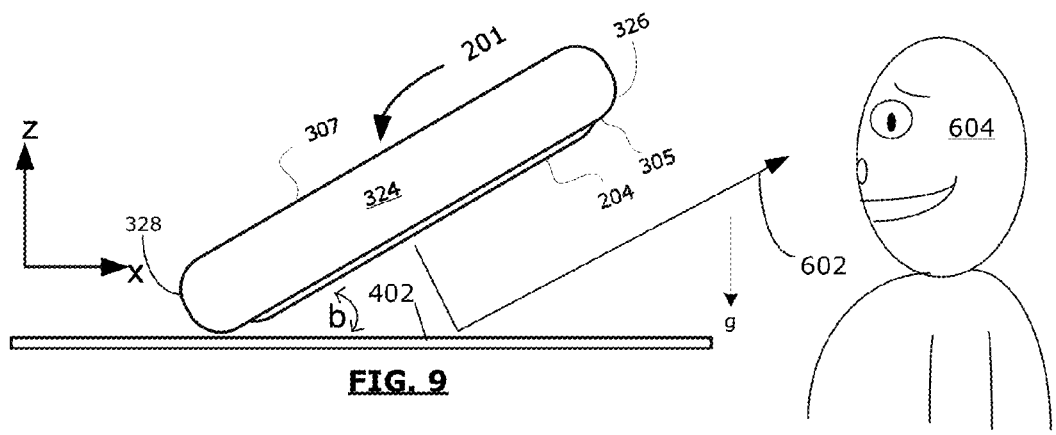
FIG. 9 is a side view of the mobile communication device tilted a second angle with respect to the surface.
Figure 10:
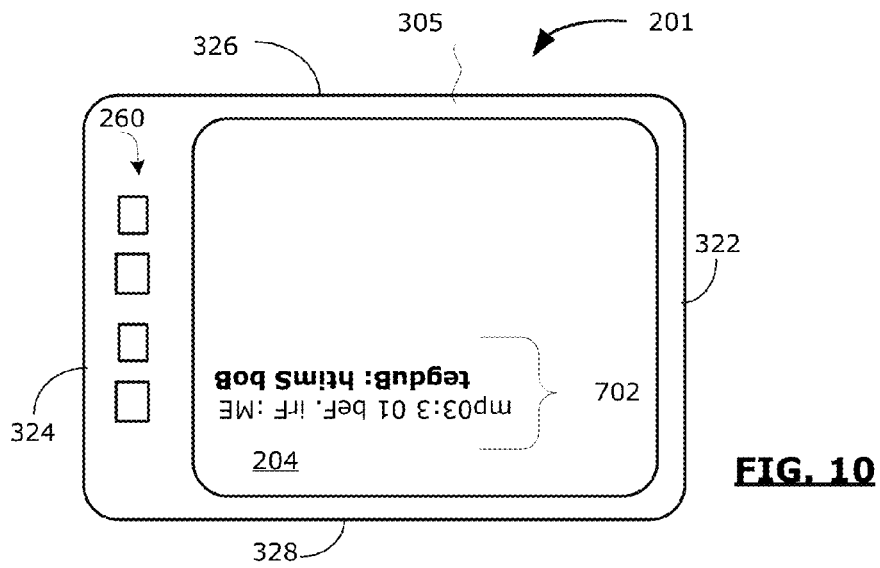
FIG. 10 is a front view of the mobile communication device showing an image presented on the device when it is in the orientation of FIG. 9.
Figure 11:
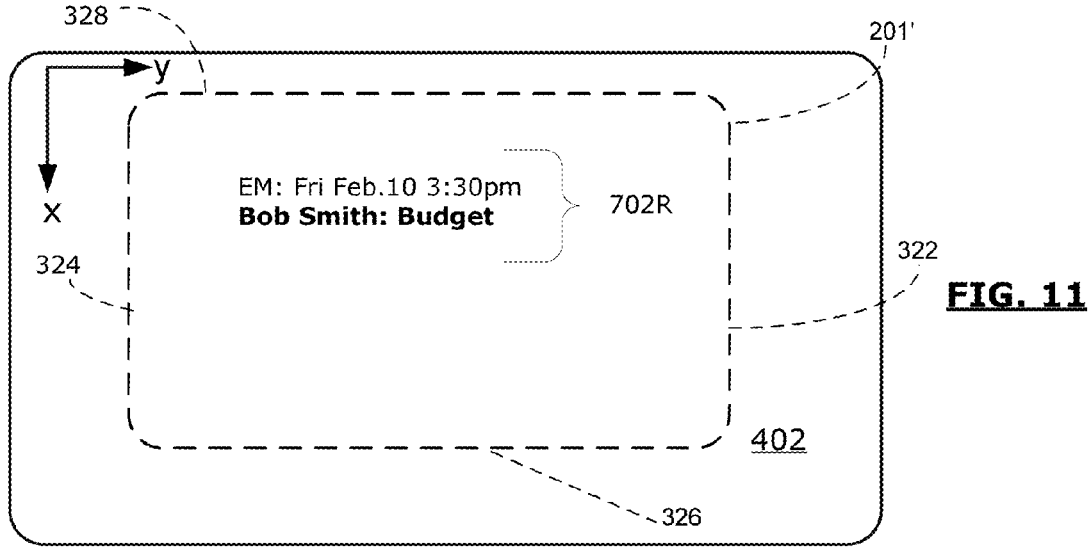
FIG. 11 is a plan view of a reflective surface reflecting the image displayed on the mobile communication device of FIG. 10.
Figure 12:
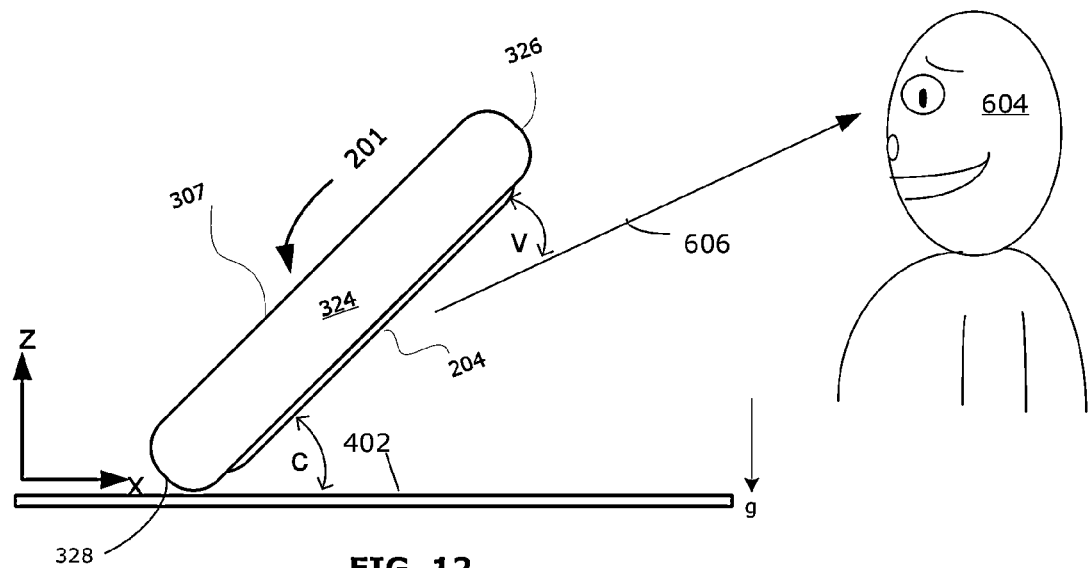
FIG. 12 is a side view of the mobile communication device tilted a third angle with respect to the surface.

Movement of the device 201 from its initial position triggers the device 201 to estimate the reflectance index of the surface it is facing. In some example embodiments, the device 201 is configured to require a further trigger such as a pending message notification to activate the surface reflection estimation system. In some embodiments, the surface reflection estimation system discriminates between specific types or ranges of movement. For example, a tilting movement such as shown in FIG. 6 of the device to a position with a tilt angle "a" within a predefined range for a predetermined duration will result in the surface reflection estimation system calculating the surface reflectance to determine if a reflective display mode is appropriate—however, the device will forgo the reflectance estimation if the orientation subsystem indicates an upward lifting of the device 201 in a horizontal position, or movement to an angle outside of the predetermined range. In some example embodiments, the brightness level or backlighting of the text displayed on the screen 204 in reflection display mode is adjusted in dependence on the relative location of the device 201 as determined by orientation subsystem 249 to the reflecting surface 402. For example, referring to FIGS. 6 to 9, at a small tilt angle "a" as shown in FIG. 6 the backlighting of display screen 204 is brighter than the backlighting used at a larger tilt angle "b" as shown in FIG. 9. In at least some uses, adjusting the brightness can provide greater privacy as the reflecting surface 402 and screen 204 are both more exposed to other persons at the wider angle "b" rather than tilt angle "a", thus the reduced brightness at angle "b" makes the image harder to view by third parties. In some example embodiments, the displayed text may be displayed as white characters and the background presented as black or dark in the reflective display mode—in such examples, the brightness of the characters could be decreased when moving from tilt angle "a" to "b". Similarly, the brightness could be adjusted in dependence on the reflectance index. In some example embodiments, the reflectance estimation system can be used to control features other than message notifications. For example, in some embodiments arrival of an incoming message or phone call or occurrence of a calendar or task event reminder, the device 201 may be configured to flash a ring border region or other region of the display screen 204 to provide a notification of the new message or call or event reminder when a new event occurs while the device is in a face down position. In such embodiments, the display screen and device housing is configured so that sufficient light leaks out from the side edges of the device, either directly or from reflection off the support surface 204 such that the flashing can be visibly detected by a device user. In some examples, the flashed notification "ring" can be color coded to indicate the type of event the ring is being generated or the identity of the party from whom a new message or call is received from, or a combination of both. In some examples, the brightness of the flashed region can be determined in dependence on the reflectance index of the surface that the stationary device is laying on, with the reflectance index being determined based on the device position (as determined by the orientation subsystem 249) and light intensity sensors such as the IR sensors 1605A 1604B. In some examples, the brightness of the flashed region can be reduced on higher reflecting surfaces so as to be more discrete. In some example embodiments, the sensed light information that is combined with location information may be obtained by a camera sensor rather than one or more IR sensors, with the display screen or a forward facing camera flash used as a light emitter.

Figure 17:
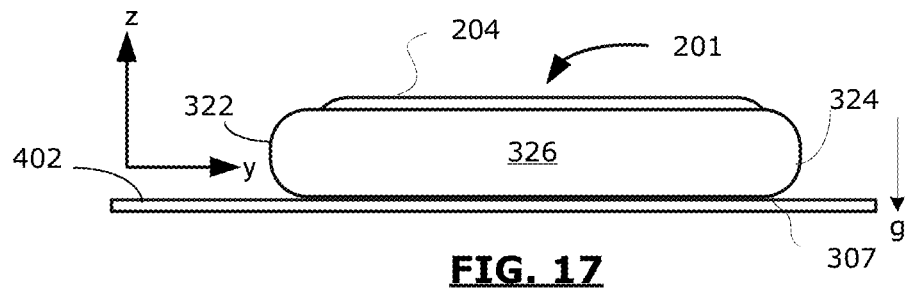
FIG. 17 is an end view of the mobile communication device face up on a support surface.
Figure 18:
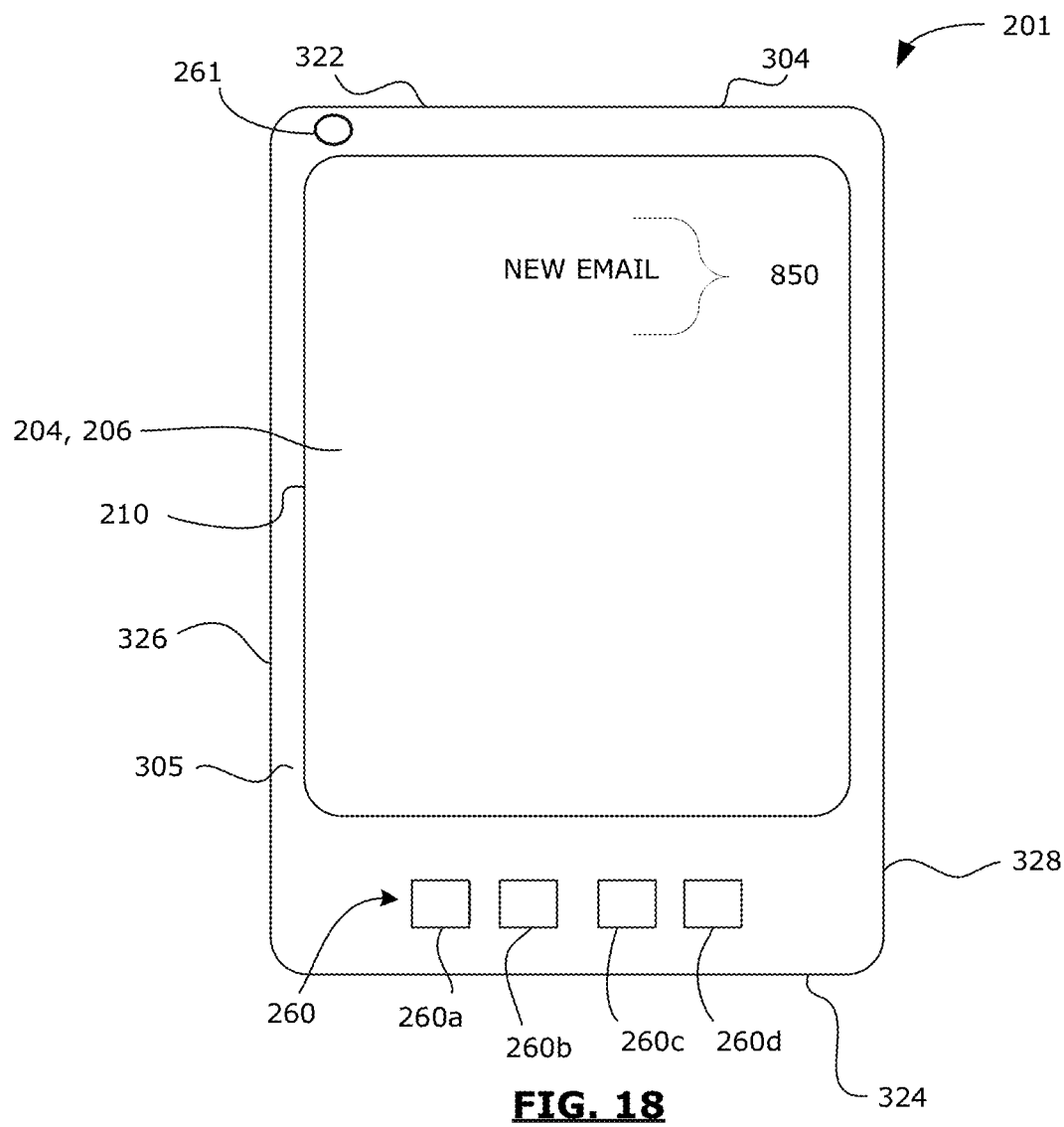
FIG. 18 is a front view of the mobile communication device showing an image presented on the device when it is in the orientation of FIG. 17.

In some example embodiments, the tilt notification message display modes are applied such that privacy can be facilitated on a face-up electronic device 201. In this regard, FIGS. 17-24 illustrate four display screen-up tilt-dependent display modes for device 201 that operate similar to the face-down display modes described above except for differences that will be apparent from the Figures and present description. FIG. 17 shows device 201 in a stationary position, resting on support surface 402 with display screen 204 facing upwards. FIG. 18 shows front of the display screen 204 in its face up position. When processor 240 detects a notification message trigger (a new email message in the illustrated embodiment) when the device 201 is in a stationary face up position the processor 240 causes a new notification message indicator to be generated—the new notification message indicator could take a form similar to that discussed above—for example a flashing LED 261 located on a visible surface of the device. However, as the display screen 204 is visible it can alternatively or also be used in a face up display mode to provide a new message indicator, including for example by displaying a basic message 850 that indicates the type of new message that the new notification message is associated with but does not include any other content of the new notification message 370.

Figure 19:
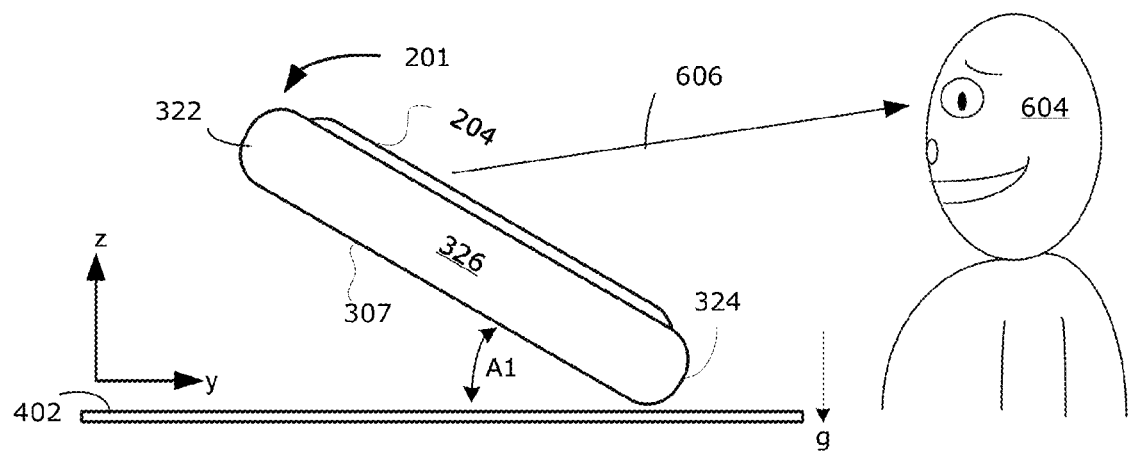
FIG. 19 is an end view of the mobile communication device tilted a first angle with respect to the surface.
Figure 20:
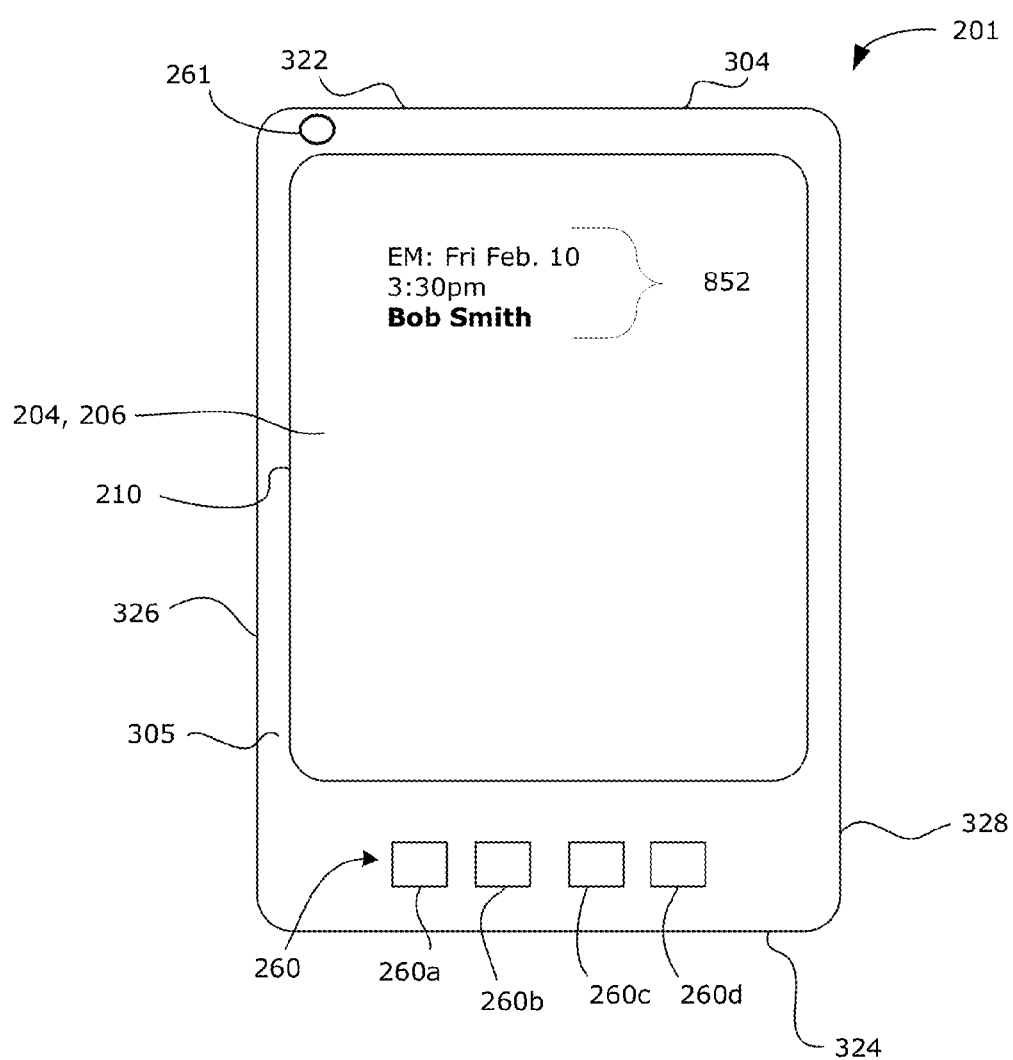
FIG. 20 is a front view of the mobile communication device showing an image presented on the device when it is in the orientation of FIG. 19.

The processor 240 monitors the face up device 201 to determine if the device 201 is tilted a threshold angle "A1"

from its stationary position. In particular, referring to the embodiment of FIG. 17, the processor 240 is effectively monitoring to see if a device user 604 tilts the device upwards on the support surface 402. More specifically, based on input from orientation subsystem 249, the processor 240 detects when the device 201 is tilted at least "A1" degrees relative to a horizontal axis that is parallel to the viewing surface of the display screen 204. In FIG. 19, the tilt axis runs into the paper along the Y axis, and is generally along the device side edge 324—thus the processor 204 monitors to determine if the edge of the device 201 that is furthest to a device user 604 (edge 322 in FIG. 19) is being tilted up while the edge of the device closest to the user (edge 324 in FIG. 19) remains substantially resting on the support surface 402. Once the threshold tilt angle "A1" is reached, the processor 240 causes selected information 852 from the notification message 370 to be displayed in a first notification message display mode on the display screen as shown in FIG. 20. In the example embodiment, the displayed information 852 includes the time field, message type field, and sender field information from the associated notification message 370, but does not include the subject or content fields.

Figure 21:
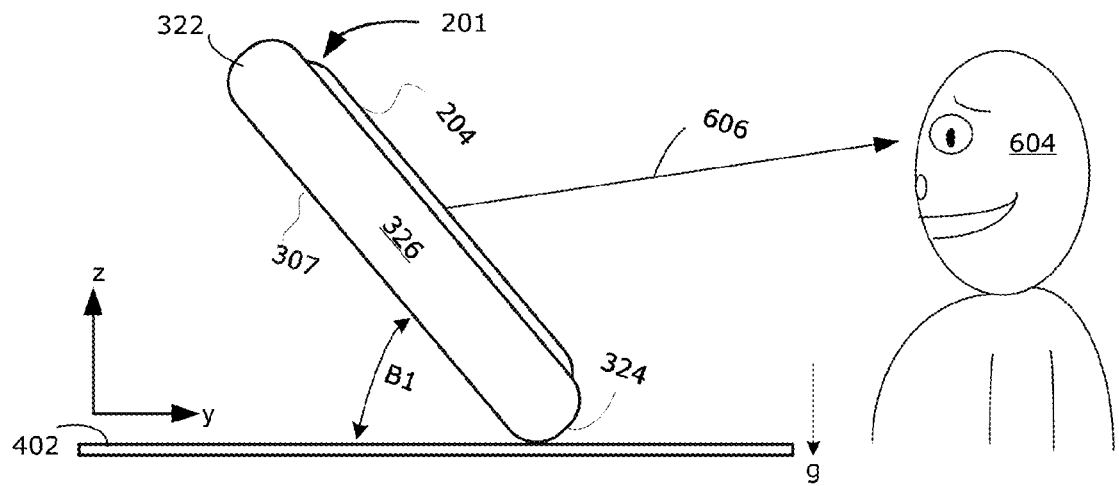
FIG. 21 is an end view of the mobile communication device tilted a second angle with respect to the surface.
Figure 22:
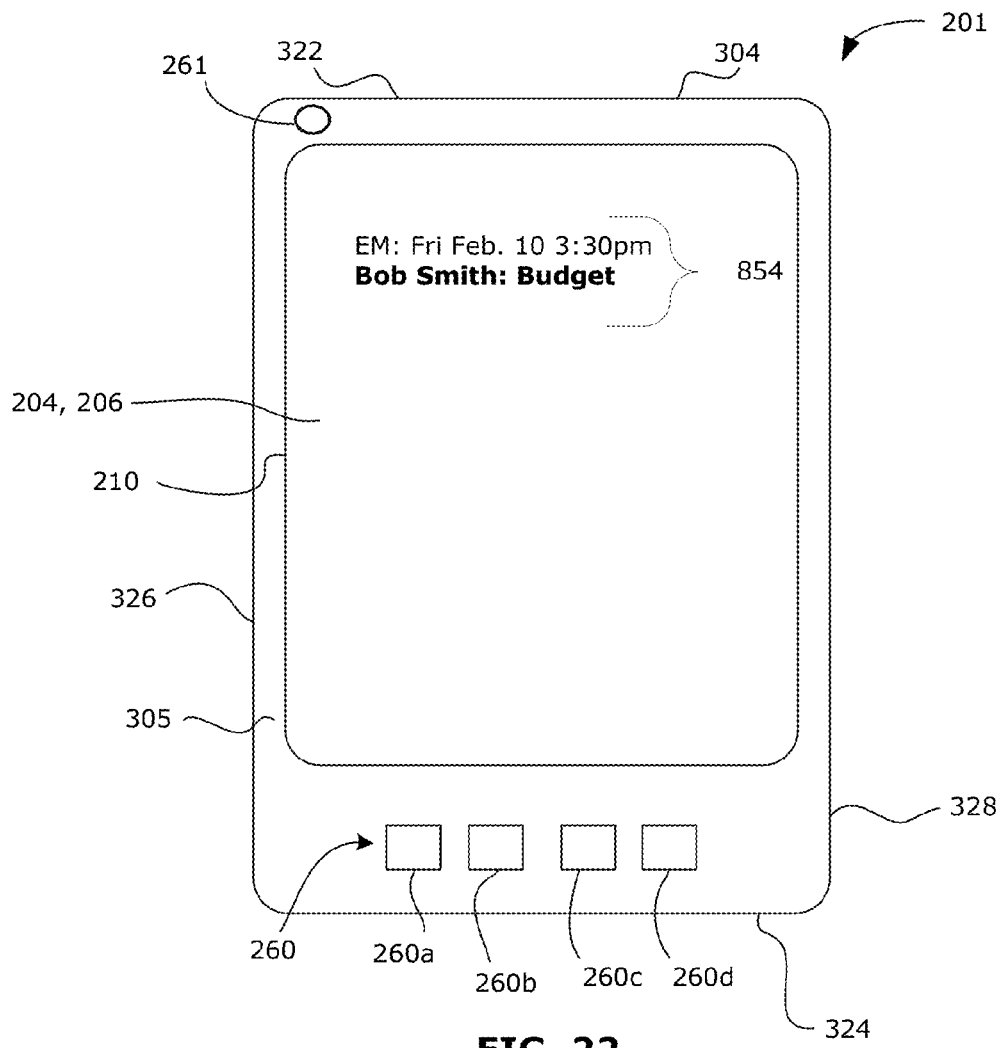
FIG. 22 is a front view of the mobile communication device showing an image presented on the device when it is in the orientation of FIG. 21.
Figure 23:
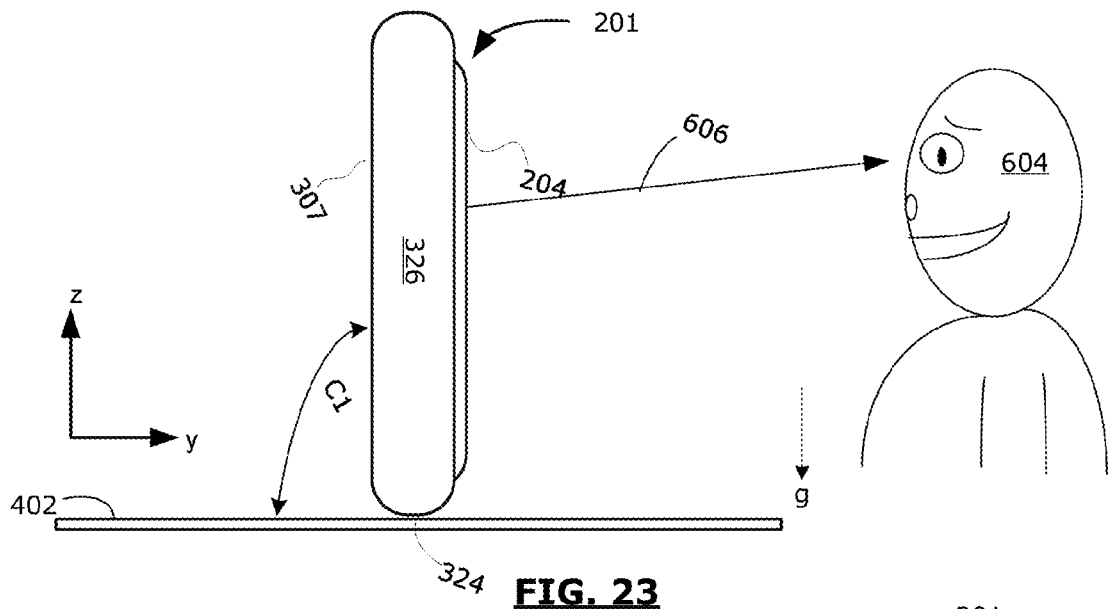
FIG. 23 is an end view of the mobile communication device tilted a third angle with respect to the surface.
Figure 24:
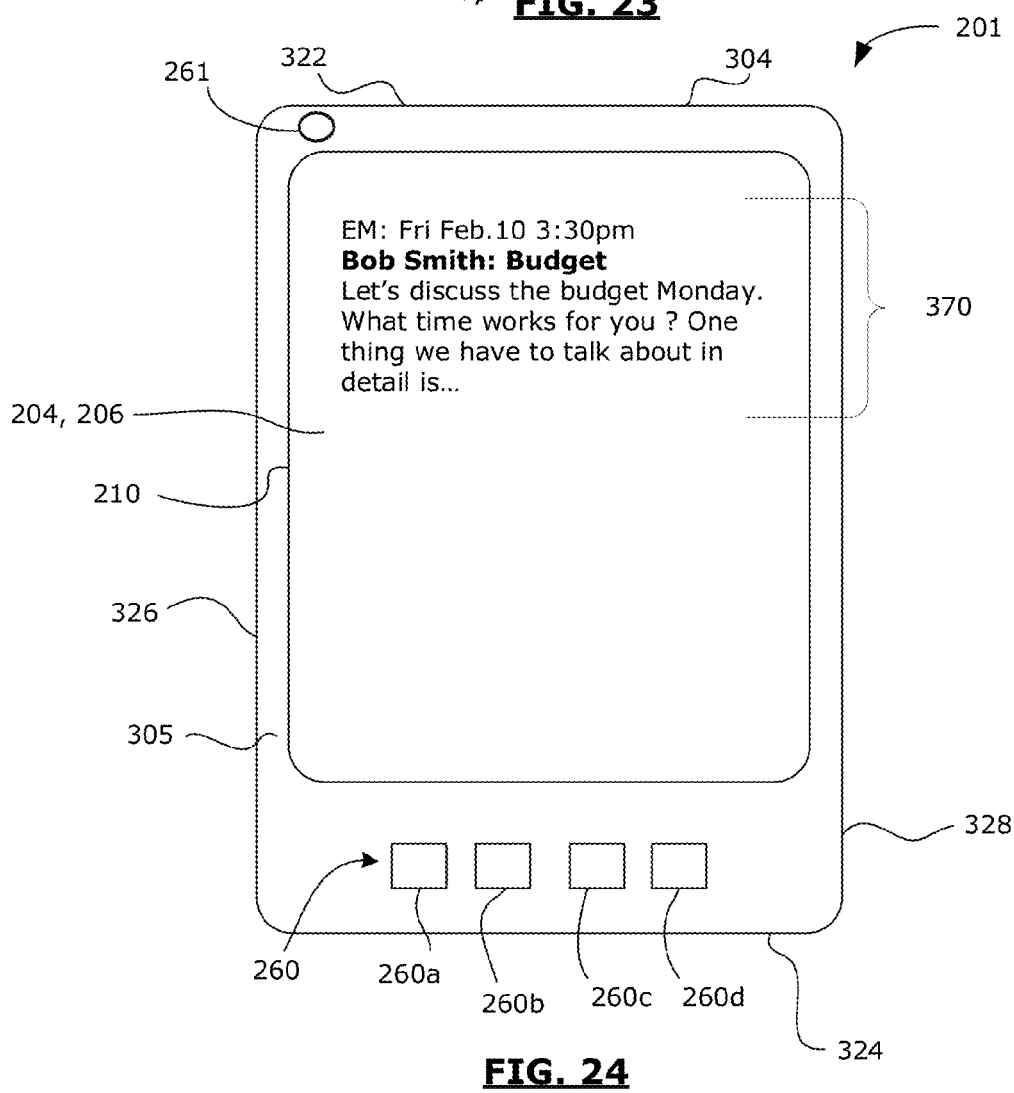
FIG. 24 is a front view of the mobile communication device showing an image presented on the device when it is in the orientation of FIG. 23.
Figure 25:
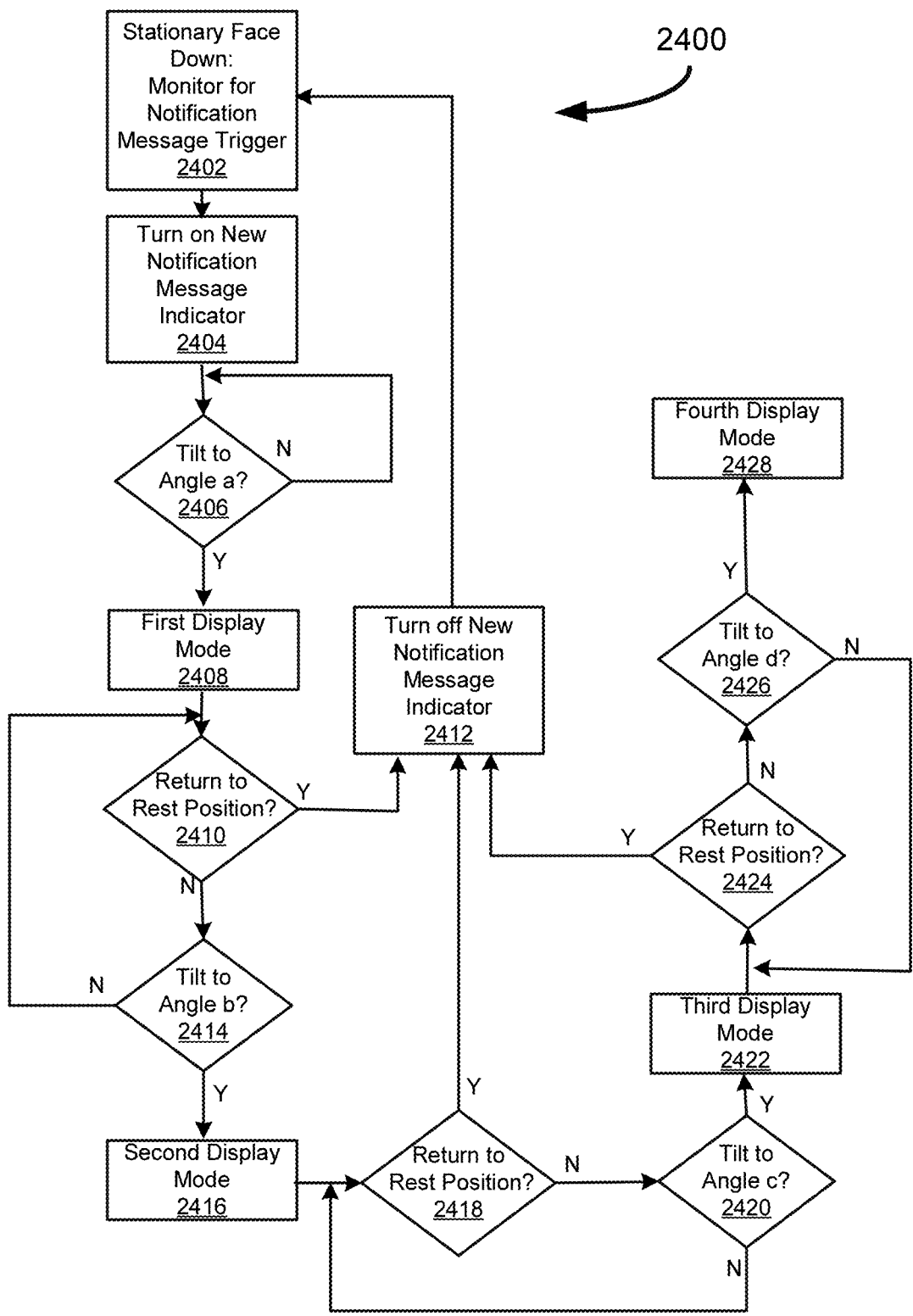
FIG. 25 is a flow diagram representing a notification message display process corresponding to FIGS. 4-15.

Referring to FIGS. 21 and 22, tilting the device 201 further to a threshold angle "B1" causes the displayed information to be modified and displayed in a second display mode. In particular, in the illustrated embodiment, the displayed information 854 in FIGS. 21 and 22 at tilt angle "B1" is the same as at the smaller tilt angle "A1", however the subject field information has been added.

In an example embodiment if the face up device 201 is tilted to yet a further threshold tilt angle "C1" the displayed notification message information is modified again and displayed in a third display mode. In particular, referring to FIGS. 23 and 24, the entire notification message 370 is displayed, such that the content field is added to the displayed information.

Thus, the display screen up notification message viewing process described above allows a device user to discretely view notification messages and progress through a series of viewing modes that are dependent on the device tilt angle in order to control the manner and amount of information displayed by the device 201.

By way of non limiting example, angle "A1" could be between 1 and 30 degrees; angle "B1" between 10 and 30 degrees greater than angle "A1"; and angle "C1" between 10 and 30 degrees greater than angle "B1". In some example embodiments, the threshold angles have can be user configured to vary from preset default values. In some example embodiments the starting position of the device may not be completely horizontal—for example the device 201 could be face up on an angled podium. The threshold angles could in some embodiments be determined relative to the starting position or relative to a absolute horizontal or a combination thereof.

In at least some example embodiments the tilt-to view features described above enable a user to privately view message notifications with a minimum amount of device interaction as the user does not need to activate the touchscreen overlay 206 or control keys 260 to view a message notification. Accordingly, such features may in some applications reduce physical wear on the physical user interfaces of the mobile communications device 201.

In some example embodiments, movements other than tilting movements could be switch between display modes.

According to at least one example embodiment is a method of displaying notification message information on a display screen of a handheld electronic device that includes determining if the handheld electronic device is tilted a first threshold relative to a first orientation and displaying in response to the tilting at least some of the notification message information, and then determining if the handheld electronic device is tilted further to a second threshold and changing the display of the notification message information on the display screen in response to the further tilting.

While the present disclosure is primarily described in terms of methods, a person of ordinary skill in the art will understand that the present disclosure is also directed to various apparatus such as a handheld electronic device including components for performing at least some of the aspects and features of the described methods, be it by way of hardware components, software or any combination of the two, or in any other manner. Moreover, an article of manufacture for use with the apparatus, such as a pre-recorded storage device or other similar computer readable medium including program instructions recorded thereon, or a computer data signal carrying computer readable program instructions may direct an apparatus to facilitate the practice of the described methods. It is understood that such apparatus, articles of manufacture, and computer data signals also come within the scope of the present disclosure.

The term "computer readable medium" as used herein means any medium which can store instructions for use by or execution by a computer or other computing device including, but not limited to, a portable computer diskette, a hard disk drive (HDD), a random access memory (RAM), a read-only memory (ROM), an erasable programmable-read-only memory (EPROM) or flash memory, an optical disc such as a Compact Disc (CD), Digital Versatile Disc (DVD) or Blu-ray™ Disc, and a solid state storage device (e.g., NAND flash or synchronous dynamic RAM (SDRAM)).

The various embodiments presented above are merely examples and are in no way meant to limit the scope of this disclosure. Variations of the innovations described herein will be apparent to persons of ordinary skill in the art, such variations being within the intended scope of the present application. In particular, features from one or more of the above-described embodiments may be selected to create alternative embodiments comprised of a sub-combination of features which may not be explicitly described above. In addition, features from one or more of the above-described embodiments may be selected and combined to create alternative embodiments comprised of a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A method of estimating reflectance of a surface adjacent a handheld electronic device having an orientation sensor and a light sensor, comprising:
   estimating a location of the handheld electronic device relative to the surface in dependence on information from the orientation sensor;
   measuring light reflected from the surface with the light sensor;
   estimating a reflectance of the surface in dependence on the estimated location and measured light; and
   displaying at least one of an image and text on a display screen of the handheld electronic device so that a reflection of the at least one of the image and text can be viewed from the surface, in dependence on the estimated reflectance.

2. The method of claim 1 wherein estimating a location comprises estimating a distance of at least a portion of the handheld electronic device to the surface.

3. The method of claim 1 wherein estimating a location comprises estimating a distance of the light sensor to the surface.

4. The method of claim 1 wherein estimating a location of the handheld electronic device relative to the surface comprises estimating a tilt angle of a display screen of the device relative to the surface.

5. The method of claim 1 wherein measuring light reflected from the surface comprises emitting light towards the surface from a light emitter located on the device.

6. The method of claim 5 wherein the light emitter comprises an infrared (IR) emitter on the device.

7. The method of claim 5 wherein the light emitter comprises the display screen of the device.

8. The method of claim 5 wherein the light emitter comprises a camera flash of the device.

9. The method of claim 1 wherein the light sensor comprises an IR sensor.

10. The method of claim 9 wherein the light sensor comprises a pair of IR sensors.

11. The method of claim 1 wherein the light sensor comprises a camera sensor.

12. The method of claim 1 comprising displaying further information on the display screen of the device in dependence on the estimated reflectance.

13. The method of claim 1 wherein one or more of an orientation, brightness or position of the displayed information is determined in dependence on the estimated reflectance.

14. A handheld electronic device comprising:
an orientation sensor;
a display screen;
a light sensor; and
a processor configured for:
estimating a location of the handheld electronic device relative to a surface in dependence on information from the orientation sensor;
measuring light reflected from the surface with the light sensor;
estimating a reflectance of the surface in dependence on the estimated location and measured light; and
displaying at least one of an image and text on the display screen so that a reflection of the at least one of the image and text can be viewed from the surface, in dependence on the estimated reflectance.

15. The handheld electronic device of claim 14 wherein estimating a location comprises estimating a distance of at least a portion of the handheld electronic device to the surface.

16. The handheld electronic device of claim 15 wherein estimating a location comprises estimating a distance of the light sensor to the surface.

17. The handheld electronic device of claim 14 wherein estimating a location of the handheld electronic device relative to the surface comprises estimating a tilt angle of a display screen of the device relative to the surface.

18. The handheld electronic device of claim 14 wherein measuring light reflected from the surface comprises emitting light towards the surface from a light emitter located on the device.

19. The handheld electronic device of claim 18 wherein the light emitter comprises an infrared (IR) emitter on the device.

20. A non-transitory computer readable medium having tangibly stored thereon computer-executable instructions that, when executed by a processor of a handheld electronic device, cause the handheld electronic device to:
estimate a location of the handheld electronic device relative to a surface adjacent the handheld electronic device, in dependence on information from an orientation sensor of the handheld electronic device;
measure light reflected from the surface with a light sensor of the handheld electronic device;
estimate a reflectance of the surface in dependence on the estimated location and measured light; and
display at least one of an image and text on a display screen of the handheld electronic device so that a reflection of the at least one of the image and text can be viewed from the surface, in dependence on the estimated reflectance.

* * * * *